United States Patent
Phelan et al.

(10) Patent No.: US 9,095,321 B2
(45) Date of Patent: Aug. 4, 2015

(54) CRYOTHERAPEUTIC DEVICES HAVING INTEGRAL MULTI-HELICAL BALLOONS AND METHODS OF MAKING THE SAME

(71) Applicant: Medtronic Ardian Luxembourg S.a.r.l., Luxembourg (LU)

(72) Inventors: Jim Phelan, Ballybrit (IE); Stephen Nash, County of Limerick (IE)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 14 days.

(21) Appl. No.: 13/683,623

(22) Filed: Nov. 21, 2012

(65) Prior Publication Data

US 2014/0142666 A1    May 22, 2014

(51) Int. Cl.
  *A61B 18/02*    (2006.01)
  *A61B 18/00*    (2006.01)
  *A61B 17/00*    (2006.01)

(52) U.S. Cl.
  CPC ....... *A61B 18/02* (2013.01); *A61B 2017/00526* (2013.01); *A61B 2018/0022* (2013.01); *A61B 2018/00404* (2013.01); *A61B 2018/00434* (2013.01); *A61B 2018/00511* (2013.01); *A61B 2018/0212* (2013.01); *A61B 2018/0262* (2013.01); *A61B 2018/0287* (2013.01)

(58) Field of Classification Search
  CPC ..................... A61B 18/02; A61B 2018/00005; A61B 2018/00011; A61B 2018/00017; A61B 2018/00023; A61B 2018/0212; A61B 2018/0231; A61B 2018/0262; A61B 2018/0268; A61B 2018/0275; A61B 2018/0281; A61B 2018/0287; A61B 2018/0022; A61B 2018/0025; A61M 25/1027; A61M 25/1029

USPC .............................. 606/20–26; 128/897, 898; 264/523–543, 294–296; 425/522, 526, 425/529
  See application file for complete search history.

(56) References Cited

U.S. PATENT DOCUMENTS

| | | | |
|---|---|---|---|
| 3,125,096 A | 3/1964 | Antiles et al. | |
| 3,298,371 A | 1/1967 | Lee | |
| 3,901,241 A | 8/1975 | Allen, Jr. | |
| 3,924,628 A | 12/1975 | Droegemueller et al. | |

(Continued)

FOREIGN PATENT DOCUMENTS

| | | |
|---|---|---|
| CN | 201469401 | 5/2010 |
| CN | 102198015 | 9/2011 |

(Continued)

OTHER PUBLICATIONS

Beale et al., "Minimally Invasive Treatment for Varicose Veins: A Review of Endovenous Laser Treatment and Radiofrequency Ablation". Lower Extremity Wounds 3(4), 2004, 10 pages.

(Continued)

*Primary Examiner* — Carl H Layno
*Assistant Examiner* — Eugene Wu

(57) ABSTRACT

A cryotherapeutic device having an integral multi-helical balloon section and methods of making the same. A method of forming the cryotherapeutic device can include forming an extruded integral shaft having first and second substantially parallel lumens. The method can further include twisting a distal section of the shaft such that the first and second lumens form intertwined helical portions. The first and second helical portions can be plastically enlarged to form an inflatable body configured to deliver therapeutically effective cryogenic cooling to a treatment site.

15 Claims, 13 Drawing Sheets

(56) References Cited

U.S. PATENT DOCUMENTS

| | | | |
|---|---|---|---|
| 3,935,348 | A | 1/1976 | Smith |
| 4,154,246 | A | 5/1979 | LeVeen |
| 4,169,464 | A | 10/1979 | Obrez |
| 4,275,734 | A | 6/1981 | Mitchiner |
| 4,406,656 | A | 9/1983 | Hattler et al. |
| 4,419,819 | A | 12/1983 | Dickhudt et al. |
| 4,602,624 | A | 7/1986 | Naples et al. |
| 4,649,936 | A | 3/1987 | Ungar et al. |
| 4,660,571 | A | 4/1987 | Hess et al. |
| 4,706,671 | A | 11/1987 | Weinrib |
| 4,709,698 | A | 12/1987 | Johnston et al. |
| 4,764,504 | A | 8/1988 | Johnson et al. |
| 4,781,682 | A | 11/1988 | Patel |
| 4,796,643 | A | 1/1989 | Nakazawa et al. |
| 4,819,661 | A | 4/1989 | Heil, Jr. et al. |
| 4,860,769 | A | 8/1989 | Fogarty et al. |
| 4,921,484 | A | 5/1990 | Hillstead |
| 4,957,118 | A | 9/1990 | Erlebacher |
| 4,961,377 | A | 10/1990 | Bando et al. |
| 4,976,711 | A | 12/1990 | Parins et al. |
| 4,995,868 | A | 2/1991 | Brazier |
| 5,002,067 | A | 3/1991 | Berthelsen et al. |
| 5,011,488 | A | 4/1991 | Ginsburg |
| 5,016,808 | A | 5/1991 | Heil, Jr. et al. |
| 5,052,998 | A | 10/1991 | Zimmon |
| 5,071,407 | A | 12/1991 | Termin et al. |
| 5,108,390 | A | 4/1992 | Potocky et al. |
| 5,108,525 | A * | 4/1992 | Gharibadeh ................ 156/86 |
| 5,133,365 | A | 7/1992 | Heil, Jr. et al. |
| 5,156,151 | A | 10/1992 | Imran |
| 5,163,928 | A | 11/1992 | Hobbs et al. |
| 5,188,602 | A | 2/1993 | Nichols |
| 5,188,619 | A | 2/1993 | Myers |
| 5,190,539 | A | 3/1993 | Fletcher et al. |
| 5,209,723 | A | 5/1993 | Twardowski et al. |
| 5,228,442 | A | 7/1993 | Imran |
| 5,239,999 | A | 8/1993 | Imran |
| 5,249,585 | A | 10/1993 | Turner et al. |
| 5,263,492 | A | 11/1993 | Voyce |
| 5,263,493 | A | 11/1993 | Avitall |
| 5,279,299 | A | 1/1994 | Imran |
| 5,296,510 | A | 3/1994 | Yamada et al. |
| 5,300,068 | A | 4/1994 | Rosar et al. |
| 5,300,099 | A | 4/1994 | Rudie |
| 5,308,323 | A | 5/1994 | Sogawa et al. |
| 5,318,525 | A | 6/1994 | West et al. |
| 5,324,284 | A | 6/1994 | Imran |
| 5,327,905 | A | 7/1994 | Avitall |
| 5,334,181 | A | 8/1994 | Rubinsky et al. |
| 5,342,301 | A | 8/1994 | Saab |
| 5,345,031 | A | 9/1994 | Schwartz et al. |
| 5,345,936 | A | 9/1994 | Pomeranz et al. |
| 5,354,297 | A | 10/1994 | Avitall |
| 5,358,514 | A | 10/1994 | Schulman et al. |
| 5,365,926 | A | 11/1994 | Desai |
| 5,368,591 | A | 11/1994 | Lennox et al. |
| 5,383,856 | A | 1/1995 | Bersin |
| 5,387,233 | A | 2/1995 | Alferness et al. |
| 5,397,304 | A | 3/1995 | Truckai |
| 5,397,339 | A | 3/1995 | Desai |
| 5,405,374 | A | 4/1995 | Stein |
| 5,411,546 | A | 5/1995 | Bowald et al. |
| 5,417,355 | A | 5/1995 | Broussalian et al. |
| 5,423,744 | A | 6/1995 | Gencheff et al. |
| 5,425,364 | A | 6/1995 | Imran |
| 5,462,545 | A | 10/1995 | Wang et al. |
| 5,476,495 | A | 12/1995 | Kordis et al. |
| 5,476,498 | A | 12/1995 | Ayers |
| 5,484,400 | A | 1/1996 | Edwards et al. |
| 5,487,385 | A | 1/1996 | Avitall |
| 5,487,757 | A | 1/1996 | Truckai et al. |
| 5,497,774 | A | 3/1996 | Swartz et al. |
| 5,507,743 | A | 4/1996 | Edwards et al. |
| 5,509,909 | A | 4/1996 | Moy |
| 5,523,092 | A | 6/1996 | Hanson et al. |
| 5,529,820 | A | 6/1996 | Nomi et al. |
| 5,545,193 | A | 8/1996 | Fleischman et al. |
| 5,545,200 | A | 8/1996 | West et al. |
| 5,545,475 | A | 8/1996 | Korleski |
| 5,549,661 | A | 8/1996 | Kordis et al. |
| 5,564,440 | A | 10/1996 | Swartz et al. |
| 5,571,147 | A | 11/1996 | Sluijter et al. |
| 5,575,766 | A | 11/1996 | Swartz et al. |
| 5,575,810 | A | 11/1996 | Swanson et al. |
| 5,582,609 | A | 12/1996 | Swanson et al. |
| 5,588,964 | A | 12/1996 | Imran et al. |
| 5,591,132 | A | 1/1997 | Carrie |
| 5,599,345 | A | 2/1997 | Edwards et al. |
| 5,609,151 | A | 3/1997 | Mulier et al. |
| 5,617,854 | A | 4/1997 | Munsif |
| 5,624,392 | A | 4/1997 | Saab |
| 5,626,576 | A | 5/1997 | Janssen |
| 5,628,775 | A | 5/1997 | Jackson et al. |
| 5,636,634 | A | 6/1997 | Kordis et al. |
| 5,637,090 | A | 6/1997 | McGee et al. |
| 5,642,736 | A | 7/1997 | Avitall |
| 5,672,174 | A | 9/1997 | Gough et al. |
| 5,676,662 | A | 10/1997 | Fleischhacker et al. |
| 5,680,860 | A | 10/1997 | Imran |
| 5,681,280 | A | 10/1997 | Rusk et al. |
| 5,687,723 | A | 11/1997 | Avitall |
| 5,688,266 | A | 11/1997 | Edwards et al. |
| 5,690,611 | A | 11/1997 | Swartz et al. |
| 5,697,928 | A | 12/1997 | Walcott et al. |
| 5,700,282 | A | 12/1997 | Zabara |
| 5,707,400 | A | 1/1998 | Terry, Jr. et al. |
| 5,709,874 | A | 1/1998 | Hanson et al. |
| 5,715,818 | A | 2/1998 | Swartz et al. |
| 5,722,401 | A | 3/1998 | Pietroski et al. |
| 5,725,512 | A | 3/1998 | Swartz et al. |
| 5,727,555 | A | 3/1998 | Chait |
| 5,730,127 | A | 3/1998 | Avitall |
| 5,730,741 | A | 3/1998 | Horzewski et al. |
| 5,755,760 | A | 5/1998 | Maguire et al. |
| 5,755,761 | A | 5/1998 | Obino |
| 5,758,505 | A | 6/1998 | Dobak, III et al. |
| 5,772,590 | A | 6/1998 | Webster, Jr. |
| 5,792,415 | A * | 8/1998 | Hijlkema ................ 264/530 |
| 5,807,391 | A | 9/1998 | Wijkamp |
| 5,807,395 | A | 9/1998 | Mulier et al. |
| 5,814,028 | A | 9/1998 | Swartz et al. |
| 5,823,955 | A | 10/1998 | Kuck et al. |
| 5,827,242 | A | 10/1998 | Follmer et al. |
| 5,827,268 | A | 10/1998 | Laufer |
| 5,837,003 | A | 11/1998 | Ginsburg |
| 5,842,984 | A | 12/1998 | Avitall |
| 5,846,355 | A | 12/1998 | Spencer et al. |
| 5,853,389 | A * | 12/1998 | Hijlkema ............... 604/103.07 |
| 5,860,920 | A | 1/1999 | McGee et al. |
| 5,860,970 | A | 1/1999 | Goddard et al. |
| 5,860,974 | A | 1/1999 | Abele |
| 5,865,787 | A | 2/1999 | Shapland et al. |
| 5,865,815 | A | 2/1999 | Tihon |
| 5,868,735 | A | 2/1999 | Lafontaine |
| 5,871,523 | A | 2/1999 | Fleischman et al. |
| 5,871,531 | A | 2/1999 | Struble |
| 5,873,865 | A | 2/1999 | Horzewski et al. |
| 5,879,295 | A | 3/1999 | Li et al. |
| 5,882,346 | A | 3/1999 | Pomeranz et al. |
| 5,893,885 | A | 4/1999 | Webster et al. |
| 5,902,299 | A | 5/1999 | Jayaraman |
| 5,910,129 | A | 6/1999 | Koblish et al. |
| 5,931,848 | A | 8/1999 | Saadat |
| 5,938,694 | A | 8/1999 | Jaraczewski et al. |
| 5,941,823 | A | 8/1999 | Chait |
| 5,944,710 | A | 8/1999 | Dev et al. |
| 5,951,471 | A | 9/1999 | de la Rama et al. |
| 5,954,719 | A | 9/1999 | Chen et al. |
| 5,957,961 | A | 9/1999 | Maguire et al. |
| 5,968,085 | A | 10/1999 | Morris et al. |
| 5,971,979 | A | 10/1999 | Joye et al. |
| 5,972,026 | A | 10/1999 | Laufer et al. |
| 5,980,516 | A | 11/1999 | Mulier et al. |
| 5,983,141 | A | 11/1999 | Sluijter et al. |

(56) References Cited

U.S. PATENT DOCUMENTS

| | | |
|---|---|---|
| 5,993,462 A | 11/1999 | Pomeranz et al. |
| 5,997,526 A | 12/1999 | Giba et al. |
| 6,004,269 A | 12/1999 | Crowley et al. |
| 6,004,348 A | 12/1999 | Banas et al. |
| 6,009,877 A | 1/2000 | Edwards |
| 6,012,457 A | 1/2000 | Lesh |
| 6,024,752 A | 2/2000 | Horn et al. |
| 6,032,077 A | 2/2000 | Pomeranz |
| 6,042,578 A | 3/2000 | Dinh et al. |
| 6,048,329 A | 4/2000 | Thompson et al. |
| 6,064,902 A | 5/2000 | Haissaguerre et al. |
| 6,066,134 A | 5/2000 | Eggers et al. |
| 6,071,729 A | 6/2000 | Jeffries et al. |
| 6,074,339 A | 6/2000 | Gambale et al. |
| 6,074,361 A | 6/2000 | Jacobs |
| 6,074,378 A | 6/2000 | Mouri et al. |
| 6,076,012 A | 6/2000 | Swanson et al. |
| 6,078,840 A | 6/2000 | Stokes |
| 6,078,841 A | 6/2000 | Kuzma |
| 6,090,104 A | 7/2000 | Webster, Jr. |
| 6,094,596 A | 7/2000 | Morgan |
| 6,096,036 A | 8/2000 | Bowe et al. |
| 6,099,524 A | 8/2000 | Lipson et al. |
| 6,106,522 A | 8/2000 | Fleischman et al. |
| 6,117,101 A | 9/2000 | Diederich et al. |
| 6,125,302 A | 9/2000 | Kuzma |
| 6,129,750 A | 10/2000 | Tockman et al. |
| 6,132,456 A | 10/2000 | Sommer et al. |
| 6,135,999 A | 10/2000 | Fanton et al. |
| 6,146,381 A | 11/2000 | Bowe et al. |
| 6,149,620 A | 11/2000 | Baker et al. |
| 6,161,048 A | 12/2000 | Sluijter et al. |
| 6,161,049 A | 12/2000 | Rudie et al. |
| 6,161,543 A | 12/2000 | Cox et al. |
| 6,164,283 A | 12/2000 | Lesh |
| 6,190,356 B1 | 2/2001 | Bersin |
| 6,214,002 B1 | 4/2001 | Fleischman et al. |
| 6,219,577 B1 | 4/2001 | Brown, III et al. |
| 6,223,070 B1 | 4/2001 | Chait |
| 6,224,592 B1 | 5/2001 | Eggers et al. |
| 6,228,109 B1 | 5/2001 | Tu et al. |
| 6,237,355 B1 | 5/2001 | Li |
| 6,241,722 B1 | 6/2001 | Dobak et al. |
| 6,246,912 B1 | 6/2001 | Sluijter et al. |
| 6,270,496 B1 | 8/2001 | Bowe et al. |
| 6,273,886 B1 | 8/2001 | Edwards et al. |
| 6,280,441 B1 | 8/2001 | Ryan |
| 6,283,951 B1 | 9/2001 | Flaherty et al. |
| 6,283,959 B1 | 9/2001 | Lalonde et al. |
| 6,290,696 B1 | 9/2001 | Lafontaine |
| 6,292,695 B1 | 9/2001 | Webster, Jr. et al. |
| 6,308,090 B1 | 10/2001 | Tu et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,325,797 B1 | 12/2001 | Stewart et al. |
| 6,355,029 B1 | 3/2002 | Joye et al. |
| 6,364,904 B1 | 4/2002 | Smith |
| 6,385,472 B1 | 5/2002 | Hall et al. |
| 6,405,732 B1 | 6/2002 | Edwards et al. |
| 6,409,742 B1 | 6/2002 | Fulton, III et al. |
| 6,413,255 B1 | 7/2002 | Stern |
| 6,430,426 B2 | 8/2002 | Avitall |
| 6,432,102 B2 | 8/2002 | Joye et al. |
| 6,442,415 B1 | 8/2002 | Bis et al. |
| 6,451,045 B1 | 9/2002 | Walker et al. |
| 6,468,297 B1 | 10/2002 | Williams et al. |
| 6,480,747 B2 | 11/2002 | Schmidt |
| 6,488,679 B1 | 12/2002 | Swanson et al. |
| 6,496,737 B2 | 12/2002 | Rudie et al. |
| 6,497,703 B1 | 12/2002 | Korteling et al. |
| 6,500,174 B1 | 12/2002 | Maguire et al. |
| 6,506,189 B1 | 1/2003 | Rittman, III et al. |
| 6,511,492 B1 | 1/2003 | Rosenbluth et al. |
| 6,514,226 B1 | 2/2003 | Levin et al. |
| 6,514,245 B1 | 2/2003 | Williams et al. |
| 6,514,249 B1 | 2/2003 | Maguire et al. |
| 6,517,533 B1 | 2/2003 | Swaminathan |
| 6,522,926 B1 | 2/2003 | Kieval et al. |
| 6,527,739 B1 | 3/2003 | Bigus et al. |
| 6,529,756 B1 | 3/2003 | Phan et al. |
| 6,530,935 B2 | 3/2003 | Wensel et al. |
| 6,537,271 B1 | 3/2003 | Murray et al. |
| 6,540,734 B1 | 4/2003 | Chiu et al. |
| 6,542,781 B1 | 4/2003 | Koblish et al. |
| 6,546,280 B2 | 4/2003 | Osborne |
| 6,551,309 B1 | 4/2003 | LePivert |
| 6,562,031 B2 | 5/2003 | Chandrasekaran et al. |
| 6,562,034 B2 | 5/2003 | Edwards et al. |
| 6,572,612 B2 | 6/2003 | Stewart et al. |
| 6,575,933 B1 | 6/2003 | Wittenberger et al. |
| 6,592,581 B2 | 7/2003 | Bowe |
| 6,602,242 B1 | 8/2003 | Fung et al. |
| 6,602,247 B2 | 8/2003 | Lalonde |
| 6,605,061 B2 | 8/2003 | VanTassel et al. |
| 6,607,520 B2 | 8/2003 | Keane |
| 6,610,046 B1 | 8/2003 | Usami et al. |
| 6,610,083 B2 | 8/2003 | Keller et al. |
| 6,613,046 B1 | 9/2003 | Jenkins et al. |
| 6,616,624 B1 | 9/2003 | Kieval |
| 6,622,731 B2 | 9/2003 | Daniel et al. |
| 6,623,515 B2 | 9/2003 | Mulier et al. |
| 6,628,976 B1 | 9/2003 | Fuimaono et al. |
| 6,635,054 B2 | 10/2003 | Fjield et al. |
| 6,648,879 B2 | 11/2003 | Joye et al. |
| 6,652,517 B1 | 11/2003 | Hall et al. |
| 6,666,858 B2 | 12/2003 | Lafontaine |
| 6,685,648 B2 | 2/2004 | Flaherty et al. |
| 6,692,490 B1 | 2/2004 | Edwards |
| 6,702,811 B2 | 3/2004 | Stewart et al. |
| 6,711,444 B2 | 3/2004 | Koblish |
| 6,736,835 B2 | 5/2004 | Pellegrino et al. |
| 6,745,080 B2 | 6/2004 | Koblish |
| 6,755,823 B2 | 6/2004 | Lalonde |
| 6,758,830 B1 | 7/2004 | Schaer et al. |
| 6,773,433 B2 | 8/2004 | Stewart et al. |
| 6,780,183 B2 | 8/2004 | Jimenez, Jr. et al. |
| 6,786,901 B2 | 9/2004 | Joye et al. |
| 6,802,840 B2 | 10/2004 | Chin et al. |
| 6,817,999 B2 | 11/2004 | Berube et al. |
| 6,824,543 B2 | 11/2004 | Lentz |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,875,209 B2 | 4/2005 | Zvuloni et al. |
| 6,882,886 B1 | 4/2005 | Witte et al. |
| 6,885,888 B2 | 4/2005 | Rezai |
| 6,890,329 B2 | 5/2005 | Carroll et al. |
| 6,893,436 B2 | 5/2005 | Woodard et al. |
| 6,893,438 B2 | 5/2005 | Hall et al. |
| 6,899,711 B2 | 5/2005 | Stewart et al. |
| 6,905,510 B2 | 6/2005 | Saab |
| 6,908,462 B2 | 6/2005 | Joye et al. |
| 6,909,920 B2 | 6/2005 | Lokhoff et al. |
| 6,923,808 B2 | 8/2005 | Taimisto |
| 6,939,346 B2 | 9/2005 | Kannenberg et al. |
| 6,941,953 B2 | 9/2005 | Feld et al. |
| 6,949,097 B2 | 9/2005 | Stewart et al. |
| 6,960,206 B2 | 11/2005 | Keane |
| 6,960,207 B2 | 11/2005 | Vanney et al. |
| 6,972,016 B2 | 12/2005 | Hill, III et al. |
| 6,981,382 B2 | 1/2006 | Lentz et al. |
| 7,013,169 B2 | 3/2006 | Bowe |
| 7,013,170 B2 | 3/2006 | Bowe |
| 7,058,456 B2 | 6/2006 | Pierce |
| 7,060,062 B2 | 6/2006 | Joye et al. |
| 7,081,112 B2 | 7/2006 | Joye et al. |
| 7,081,115 B2 | 7/2006 | Taimisto |
| 7,104,988 B2 | 9/2006 | Altman et al. |
| 7,110,828 B2 | 9/2006 | Kolberg et al. |
| 7,115,134 B2 | 10/2006 | Chambers |
| 7,149,574 B2 | 12/2006 | Yun et al. |
| 7,156,840 B2 | 1/2007 | Lentz et al. |
| 7,162,303 B2 | 1/2007 | Levin et al. |

(56) References Cited

U.S. PATENT DOCUMENTS

| | | |
|---|---|---|
| 7,201,738 B1 | 4/2007 | Bengmark |
| 7,211,082 B2 | 5/2007 | Hall et al. |
| 7,221,979 B2 | 5/2007 | Zhou et al. |
| 7,254,451 B2 | 8/2007 | Seifert et al. |
| 7,285,119 B2 | 10/2007 | Stewart et al. |
| 7,291,146 B2 | 11/2007 | Steinke et al. |
| 7,306,590 B2 | 12/2007 | Swanson |
| 7,311,705 B2 | 12/2007 | Sra |
| 7,357,797 B2 | 4/2008 | Ryba |
| 7,381,200 B2 | 6/2008 | Katoh et al. |
| 7,390,894 B2 | 6/2008 | Weinshilboum et al. |
| 7,395,116 B2 * | 7/2008 | Mehdizadeh et al. ........... 607/37 |
| 7,435,248 B2 | 10/2008 | Taimisto et al. |
| 7,517,349 B2 | 4/2009 | Truckai et al. |
| 7,526,343 B2 | 4/2009 | Peterson et al. |
| 7,542,808 B1 | 6/2009 | Peterson et al. |
| 7,604,631 B2 | 10/2009 | Reynolds |
| 7,617,005 B2 | 11/2009 | Demarais et al. |
| 7,637,903 B2 | 12/2009 | Lentz et al. |
| 7,641,679 B2 | 1/2010 | Joye et al. |
| 7,647,115 B2 | 1/2010 | Levin et al. |
| 7,647,124 B2 | 1/2010 | Williams |
| 7,653,438 B2 | 1/2010 | Deem et al. |
| 7,682,319 B2 | 3/2010 | Martin et al. |
| 7,717,948 B2 | 5/2010 | Demarais et al. |
| 7,729,782 B2 | 6/2010 | Williams et al. |
| 7,747,334 B2 | 6/2010 | Bly et al. |
| 7,758,571 B2 | 7/2010 | Saadat |
| 7,771,421 B2 | 8/2010 | Stewart et al. |
| 7,778,703 B2 | 8/2010 | Gross et al. |
| 7,785,289 B2 | 8/2010 | Rios et al. |
| 7,789,877 B2 | 9/2010 | Vanney |
| 7,850,685 B2 | 12/2010 | Kunis et al. |
| 7,861,725 B2 | 1/2011 | Swanson |
| 7,867,219 B2 | 1/2011 | Chambers |
| 7,881,807 B2 | 2/2011 | Schaer |
| 7,890,188 B2 | 2/2011 | Zhang et al. |
| 1,015,285 A1 | 6/2011 | Mayse et al. |
| 7,959,630 B2 | 6/2011 | Taimisto et al. |
| 7,972,327 B2 | 7/2011 | Eberl et al. |
| 8,019,435 B2 | 9/2011 | Hastings et al. |
| 1,026,392 A1 | 10/2011 | Vrba et al. |
| 1,026,408 A1 | 10/2011 | Ingle |
| 1,027,023 A1 | 11/2011 | Rizq et al. |
| 1,028,227 A1 | 11/2011 | Lafontaine |
| 8,062,284 B2 | 11/2011 | Booth |
| 1,031,990 A1 | 12/2011 | Thenuwara et al. |
| 8,088,125 B2 | 1/2012 | Lafontaine |
| 8,100,859 B2 | 1/2012 | Patterson et al. |
| 8,123,739 B2 | 2/2012 | McQueen et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,192,428 B2 | 6/2012 | Truckai et al. |
| 8,257,351 B2 | 9/2012 | Stewart et al. |
| 8,337,492 B2 | 12/2012 | Kunis et al. |
| 8,380,275 B2 | 2/2013 | Kim et al. |
| 8,473,067 B2 | 6/2013 | Hastings et al. |
| 8,475,441 B2 | 7/2013 | Babkin et al. |
| 8,480,664 B2 | 7/2013 | Watson et al. |
| 8,571,665 B2 | 10/2013 | Moffitt |
| 8,663,211 B2 | 3/2014 | Fourkas et al. |
| 8,740,895 B2 | 6/2014 | Mayse et al. |
| 8,777,943 B2 | 7/2014 | Mayse et al. |
| 2001/0005785 A1 | 6/2001 | Sachse |
| 2001/0007070 A1 | 7/2001 | Stewart et al. |
| 2001/0020174 A1 | 9/2001 | Koblish |
| 2001/0031971 A1 | 10/2001 | Dretler et al. |
| 2002/0004631 A1 | 1/2002 | Jenkins et al. |
| 2002/0004644 A1 | 1/2002 | Koblish |
| 2002/0045893 A1 | 4/2002 | Lane et al. |
| 2002/0062124 A1 | 5/2002 | Keane |
| 2002/0087208 A1 | 7/2002 | Koblish et al. |
| 2002/0120258 A1 | 8/2002 | Lalonde |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2002/0193735 A1 * | 12/2002 | Stiger ..................... 604/101.01 |
| 2003/0036752 A1 | 2/2003 | Joye et al. |
| 2003/0050681 A1 | 3/2003 | Pianca et al. |
| 2003/0060762 A1 | 3/2003 | Zvuloni et al. |
| 2003/0060858 A1 | 3/2003 | Kieval et al. |
| 2003/0074039 A1 | 4/2003 | Puskas |
| 2003/0088240 A1 | 5/2003 | Saadat |
| 2003/0088244 A1 | 5/2003 | Swanson et al. |
| 2003/0125790 A1 | 7/2003 | Fastovsky et al. |
| 2003/0153967 A1 | 8/2003 | Koblish et al. |
| 2003/0158584 A1 | 8/2003 | Cates et al. |
| 2003/0181897 A1 | 9/2003 | Thomas et al. |
| 2003/0199863 A1 | 10/2003 | Swanson et al. |
| 2003/0204187 A1 | 10/2003 | Hintringer |
| 2003/0216792 A1 | 11/2003 | Levin et al. |
| 2003/0233099 A1 | 12/2003 | Danaek et al. |
| 2004/0010289 A1 | 1/2004 | Biggs et al. |
| 2004/0024392 A1 | 2/2004 | Lewis et al. |
| 2004/0030375 A1 | 2/2004 | Pierce |
| 2004/0049181 A1 | 3/2004 | Stewart et al. |
| 2004/0082978 A1 | 4/2004 | Harrison et al. |
| 2004/0215186 A1 | 10/2004 | Cornelius et al. |
| 2005/0010095 A1 | 1/2005 | Stewart et al. |
| 2005/0080409 A1 | 4/2005 | Young et al. |
| 2005/0187579 A1 | 8/2005 | Danek et al. |
| 2005/0228460 A1 | 10/2005 | Levin et al. |
| 2005/0240117 A1 | 10/2005 | Zvuloni et al. |
| 2006/0074403 A1 | 4/2006 | Rafiee |
| 2006/0084962 A1 | 4/2006 | Joye et al. |
| 2006/0095029 A1 | 5/2006 | Young et al. |
| 2006/0100618 A1 | 5/2006 | Chan et al. |
| 2006/0135870 A1 | 6/2006 | Webler |
| 2006/0135953 A1 | 6/2006 | Kania et al. |
| 2006/0206150 A1 | 9/2006 | Demarais et al. |
| 2006/0212027 A1 | 9/2006 | Marrouche et al. |
| 2006/0241366 A1 | 10/2006 | Falwell et al. |
| 2006/0247611 A1 | 11/2006 | Abboud et al. |
| 2006/0247744 A1 | 11/2006 | Nest et al. |
| 2006/0271111 A1 | 11/2006 | Demarais et al. |
| 2007/0083194 A1 | 4/2007 | Kunis et al. |
| 2007/0129720 A1 | 6/2007 | Demarais et al. |
| 2007/0185445 A1 | 8/2007 | Nahon et al. |
| 2007/0213793 A1 * | 9/2007 | Hayes, Jr. .................... 607/105 |
| 2007/0265687 A1 | 11/2007 | Deem et al. |
| 2007/0299433 A1 | 12/2007 | Williams et al. |
| 2008/0045921 A1 | 2/2008 | Anderson et al. |
| 2008/0097398 A1 | 4/2008 | Mitelberg et al. |
| 2008/0108975 A1 | 5/2008 | Appling et al. |
| 2008/0109011 A1 | 5/2008 | Thenuwara et al. |
| 2008/0140174 A1 * | 6/2008 | Oepen et al. ................. 623/1.11 |
| 2008/0208182 A1 | 8/2008 | Lafontaine et al. |
| 2008/0255539 A1 | 10/2008 | Booth |
| 2008/0288039 A1 | 11/2008 | Reddy |
| 2008/0300584 A1 | 12/2008 | Lentz et al. |
| 2008/0300587 A1 | 12/2008 | Anderson |
| 2008/0306475 A1 | 12/2008 | Lentz et al. |
| 2008/0312644 A1 | 12/2008 | Fourkas et al. |
| 2008/0319513 A1 | 12/2008 | Pu et al. |
| 2009/0018534 A1 | 1/2009 | Taimisto et al. |
| 2009/0036948 A1 | 2/2009 | Levin et al. |
| 2009/0182316 A1 | 7/2009 | Bencini |
| 2009/0182317 A1 | 7/2009 | Bencini |
| 2009/0209949 A1 | 8/2009 | Ingle et al. |
| 2009/0281533 A1 | 11/2009 | Ingle et al. |
| 2009/0287202 A1 * | 11/2009 | Ingle et al. ..................... 606/21 |
| 2009/0299355 A1 | 12/2009 | Bencini et al. |
| 2009/0306650 A1 | 12/2009 | Govari et al. |
| 2009/0312606 A1 | 12/2009 | Dayton et al. |
| 2010/0030112 A1 | 2/2010 | Anderson et al. |
| 2010/0049184 A1 | 2/2010 | George et al. |
| 2010/0069900 A1 | 3/2010 | Shirley et al. |
| 2010/0100087 A1 | 4/2010 | Mazzone et al. |

(56) References Cited

U.S. PATENT DOCUMENTS

| | | |
|---|---|---|
| 2010/0106148 A1 | 4/2010 | Joye et al. |
| 2010/0114269 A1 | 5/2010 | Wittenberger et al. |
| 2010/0125266 A1* | 5/2010 | Deem et al. .............. 606/21 |
| 2010/0130970 A1* | 5/2010 | Williams et al. ............ 606/21 |
| 2010/0137860 A1 | 6/2010 | Demarais et al. |
| 2010/0137952 A1 | 6/2010 | Demarais et al. |
| 2010/0168777 A1 | 7/2010 | Stangenes et al. |
| 2010/0174282 A1 | 7/2010 | Demarais et al. |
| 2010/0179512 A1 | 7/2010 | Chong et al. |
| 2010/0179526 A1 | 7/2010 | Lawrence |
| 2010/0179527 A1 | 7/2010 | Watson et al. |
| 2010/0191112 A1 | 7/2010 | Demarais et al. |
| 2010/0198203 A1 | 8/2010 | Kuck et al. |
| 2010/0204692 A1 | 8/2010 | Stewart et al. |
| 2010/0222851 A1 | 9/2010 | Deem et al. |
| 2010/0222854 A1 | 9/2010 | Demarais et al. |
| 2010/0234838 A1 | 9/2010 | Watson |
| 2010/0249766 A1 | 9/2010 | Saadat |
| 2010/0256621 A1 | 10/2010 | Babkin et al. |
| 2010/0261990 A1 | 10/2010 | Gillis et al. |
| 2010/0280507 A1 | 11/2010 | Babkin et al. |
| 2011/0144639 A1 | 6/2011 | Govari |
| 2011/0160719 A1 | 6/2011 | Govari et al. |
| 2011/0306851 A1 | 12/2011 | Wang |
| 2012/0010607 A1 | 1/2012 | Malecki et al. |
| 2012/0029509 A1 | 2/2012 | Smith |
| 2012/0029510 A1 | 2/2012 | Haverkost |
| 2012/0029511 A1 | 2/2012 | Smith et al. |
| 2012/0029513 A1 | 2/2012 | Smith et al. |
| 2012/0035615 A1 | 2/2012 | Koester et al. |
| 2012/0078076 A1 | 3/2012 | Stewart et al. |
| 2012/0089047 A1 | 4/2012 | Ryba et al. |
| 2012/0101553 A1 | 4/2012 | Reddy |
| 2012/0116382 A1 | 5/2012 | Ku et al. |
| 2012/0116383 A1 | 5/2012 | Mauch et al. |
| 2012/0123261 A1 | 5/2012 | Jenson et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130360 A1 | 5/2012 | Buckley et al. |
| 2012/0130368 A1 | 5/2012 | Jenson |
| 2012/0136417 A1 | 5/2012 | Buckley et al. |
| 2012/0136418 A1 | 5/2012 | Buckley et al. |
| 2012/0143097 A1 | 6/2012 | Pike, Jr. |
| 2012/0143293 A1 | 6/2012 | Mauch et al. |
| 2012/0150267 A1 | 6/2012 | Buckley et al. |
| 2012/0172837 A1 | 7/2012 | Demarais et al. |
| 2012/0191083 A1 | 7/2012 | Moll et al. |
| 2012/0197246 A1 | 8/2012 | Mauch |
| 2012/0253336 A1 | 10/2012 | Littrup et al. |
| 2012/0277842 A1 | 11/2012 | Kunis |
| 2012/0290053 A1 | 11/2012 | Zhang et al. |
| 2012/0310065 A1 | 12/2012 | Falwell et al. |
| 2012/0310239 A1 | 12/2012 | Stewart et al. |
| 2012/0323233 A1 | 12/2012 | Maguire et al. |
| 2013/0053876 A1 | 2/2013 | Ogle |
| 2013/0085360 A1 | 4/2013 | Grunewald |
| 2013/0090637 A1 | 4/2013 | Sliwa |
| 2013/0090650 A1 | 4/2013 | Jenson et al. |
| 2013/0123770 A1 | 5/2013 | Smith |
| 2013/0165920 A1 | 6/2013 | Weber et al. |
| 2013/0165921 A1 | 6/2013 | Sutermeister et al. |
| 2013/0172872 A1 | 7/2013 | Subramaniam et al. |
| 2013/0172879 A1 | 7/2013 | Sutermeister et al. |
| 2013/0184696 A1 | 7/2013 | Fourkas et al. |
| 2013/0184773 A1 | 7/2013 | Libbus |
| 2013/0253628 A1 | 9/2013 | Chaska |
| 2013/0274614 A1 | 10/2013 | Shimada |
| 2013/0274730 A1 | 10/2013 | Anderson |
| 2013/0274731 A1 | 10/2013 | Anderson |
| 2013/0274737 A1 | 10/2013 | Wang |
| 2013/0282000 A1 | 10/2013 | Parsonage |
| 2013/0282084 A1 | 10/2013 | Mathur |
| 2013/0289686 A1 | 10/2013 | Masson |
| 2013/0304047 A1 | 11/2013 | Grunewald |
| 2013/0304052 A1 | 11/2013 | Rizq |
| 2013/0304062 A1 | 11/2013 | Chan |
| 2013/0345688 A1 | 12/2013 | Babkin |
| 2014/0046313 A1 | 2/2014 | Pederson et al. |
| 2014/0058376 A1 | 2/2014 | Horn |
| 2014/0066914 A1 | 3/2014 | Lafontaine |
| 2014/0213873 A1 | 7/2014 | Wang |
| 2014/0214018 A1 | 7/2014 | Behar et al. |
| 2014/0221805 A1 | 8/2014 | Wang |
| 2014/0243821 A1 | 8/2014 | Salahieh et al. |

FOREIGN PATENT DOCUMENTS

| | | |
|---|---|---|
| CN | 102274075 | 12/2011 |
| CN | 102488552 | 6/2012 |
| CN | 202386778 | 8/2012 |
| CN | 202426649 | 9/2012 |
| CN | 202537649 | 11/2012 |
| CN | 202538132 | 11/2012 |
| CN | 102885648 | 1/2013 |
| CN | 102885649 | 1/2013 |
| CN | 102908188 | 2/2013 |
| CN | 102908189 | 2/2013 |
| CN | 202761434 | 3/2013 |
| CN | 202843784 | 4/2013 |
| DE | 4406451 | 9/1995 |
| DE | 29909082 | 7/1999 |
| DE | 10252325 | 5/2004 |
| DE | 10257146 | 6/2004 |
| EP | 0132344 | 1/1985 |
| EP | 0132344 | 1/1986 |
| EP | 0510624 | 10/1992 |
| EP | 0655225 | 5/1995 |
| EP | 510624 | 7/1995 |
| EP | 732080 | 9/1996 |
| EP | 0779079 | 6/1997 |
| EP | 0821602 | 2/1998 |
| EP | 0868923 | 10/1998 |
| EP | 0728495 | 4/1999 |
| EP | 0916360 | 5/1999 |
| EP | 0955012 | 11/1999 |
| EP | 1042990 | 10/2000 |
| EP | 1129670 | 9/2001 |
| EP | 1164963 | 1/2002 |
| EP | 1233716 | 8/2002 |
| EP | 963191 | 8/2003 |
| EP | 757575 | 9/2003 |
| EP | 873760 | 1/2004 |
| EP | 1389477 | 2/2004 |
| EP | 779079 | 3/2004 |
| EP | 1502553 | 2/2005 |
| EP | 1559362 | 8/2005 |
| EP | 0778043 | 11/2005 |
| EP | 1042990 | 10/2006 |
| EP | 1733689 | 12/2006 |
| EP | 1802370 | 7/2007 |
| EP | 1009303 | 6/2009 |
| EP | 2208474 | 7/2010 |
| EP | 2263588 | 12/2010 |
| EP | 2519173 | 11/2012 |
| EP | 2558016 | 2/2013 |
| EP | 2598069 | 6/2013 |
| EP | 2598070 | 6/2013 |
| EP | 2598071 | 6/2013 |
| EP | 2608837 | 7/2013 |
| EP | 2664295 | 11/2013 |
| EP | 2694158 | 2/2014 |
| EP | 2759275 | 7/2014 |
| EP | 2760532 | 8/2014 |
| GB | 228367 | 2/1925 |
| GB | 1422535 | 1/1976 |
| GB | 2283678 | 5/1995 |
| GB | 2289414 | 11/1995 |
| JP | 355137141 | 10/1980 |
| SU | 718099 | 2/1980 |
| SU | 1153901 | 5/1985 |
| SU | 1329781 | 8/1987 |
| SU | 1378835 | 3/1988 |
| SU | 1771725 | 6/1990 |

(56) References Cited

FOREIGN PATENT DOCUMENTS

| | | |
|---|---|---|
| WO | WO-9115254 | 10/1991 |
| WO | WO-9220291 | 11/1992 |
| WO | WO-9421168 | 9/1994 |
| WO | WO-9513111 | 5/1995 |
| WO | WO-9520416 | 8/1995 |
| WO | WO-9525472 | 9/1995 |
| WO | WO-9600036 | 1/1996 |
| WO | WO-9632980 | 10/1996 |
| WO | WO-9638196 | 12/1996 |
| WO | WO-9717892 | 5/1997 |
| WO | WO9717892 | 5/1997 |
| WO | WO-9725011 | 7/1997 |
| WO | WO-9736548 | 10/1997 |
| WO | WO-9802201 | 1/1998 |
| WO | WO-9833469 | 8/1998 |
| WO | WO-9843530 | 10/1998 |
| WO | WO9900060 | 1/1999 |
| WO | WO-9905979 | 2/1999 |
| WO | WO-9927862 | 6/1999 |
| WO | WO-9956801 | 11/1999 |
| WO | WO-9962413 | 12/1999 |
| WO | WO 0001313 | 1/2000 |
| WO | WO-0056237 | 9/2000 |
| WO | WO-0067832 | 11/2000 |
| WO | WO-0122897 | 4/2001 |
| WO | WO-0137723 | 5/2001 |
| WO | WO-0137746 | 5/2001 |
| WO | WO-0164145 | 9/2001 |
| WO | WO-0170114 | 9/2001 |
| WO | WO-0180758 | 11/2001 |
| WO | WO-0200128 | 1/2002 |
| WO | WO-0204042 | 1/2002 |
| WO | WO-0207625 | 1/2002 |
| WO | WO-0207628 | 1/2002 |
| WO | WO-0213710 | 2/2002 |
| WO | WO-0245608 | 6/2002 |
| WO | WO-02058576 | 8/2002 |
| WO | WO-02083017 | 10/2002 |
| WO | WO-02087453 | 11/2002 |
| WO | WO-02089687 | 11/2002 |
| WO | WO-02089908 | 11/2002 |
| WO | WO-03020334 | 3/2003 |
| WO | WO-03061496 | 7/2003 |
| WO | WO-03082080 | 10/2003 |
| WO | WO-2004100813 | 11/2004 |
| WO | WO-2005030072 | 4/2005 |
| WO | WO-2005038357 | 4/2005 |
| WO | WO-2005041748 | 5/2005 |
| WO | WO-2005051216 | 6/2005 |
| WO | WO-2005070491 | 8/2005 |
| WO | WO-2005110528 | 11/2005 |
| WO | WO-2006020920 | 2/2006 |
| WO | WO-2006041881 | 4/2006 |
| WO | WO-2006065949 | 6/2006 |
| WO | WO-2006092000 | 9/2006 |
| WO | WO-2006096272 | 9/2006 |
| WO | WO-2006124177 | 11/2006 |
| WO | WO-2007001981 | 1/2007 |
| WO | WO-2007008954 | 1/2007 |
| WO | WO-2007128064 | 11/2007 |
| WO | WO-2008101244 | 8/2008 |
| WO | WO-2008131037 | 10/2008 |
| WO | WO-2009121017 | 1/2009 |
| WO | WO-2010048676 | 5/2010 |
| WO | WO-2010091701 | 8/2010 |
| WO | WO-2010120835 | 10/2010 |
| WO | WO-2011015218 | 2/2011 |
| WO | WO-2011019838 | 2/2011 |
| WO | WO-2011056684 | 5/2011 |
| WO | WO-2011082278 | 7/2011 |
| WO | WO-2011082279 | 7/2011 |
| WO | WO-2011130534 | 10/2011 |
| WO | WO-2012016135 | 2/2012 |
| WO | WO-2012016137 | 2/2012 |
| WO | WO-2012058430 | 5/2012 |
| WO | WO-2012075156 | 6/2012 |
| WO | WO-2012130337 | 10/2012 |
| WO | WO-2012131107 | 10/2012 |
| WO | WO2012148966 | 11/2012 |
| WO | WO-2012154219 | 11/2012 |
| WO | WO-2012154796 | 11/2012 |
| WO | WO-2013016203 | 1/2013 |
| WO | WO-2013028993 | 2/2013 |
| WO | WO-2013030807 | 3/2013 |
| WO | WO-2013040201 | 3/2013 |
| WO | WO-2013049601 | 4/2013 |
| WO | WO-2013074683 | 5/2013 |
| WO | WO-2013101452 | 7/2013 |
| WO | WO-2013106054 | 7/2013 |
| WO | WO2013106859 | 7/2013 |
| WO | WO2013109318 | 7/2013 |
| WO | WO2013158676 | 10/2013 |
| WO | WO2013158678 | 10/2013 |
| WO | WO2013165920 | 11/2013 |
| WO | WO2013154776 | 12/2013 |
| WO | WO-2014036160 | 3/2014 |
| WO | WO-2014036163 | 3/2014 |
| WO | WO-2014056460 | 4/2014 |
| WO | WO2014081910 | 5/2014 |

OTHER PUBLICATIONS

International Search Report and Written Opinion for International Application No. PCT/US2011/046845, mailed Dec. 16, 2011, 16 pages.

Miller, Reed, "Finding a Future for Renal Denervation With Better Controlled Trials." Pharma & Medtech Business Intelligence, Article # 01141006003, Oct. 6, 2014, 4 pages.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Doumas, Michael et al., "Renal Nerve Ablation for Resistant Hypertension: The Dust Has Not Yet Settled." The Journal of Clinical Hypertension. 2014; vol. 16, No. 6, 2 pages.

Messerli, Franz H. et al. "Renal Denervation for Resistant Hypertension: Dead or Alive?" Healio: Cardiology today's Intervention, May/Jun. 2014, 2 pages.

International Search Report, PCT/US02/07661, Aug. 13, 2002, 5 Pages.

International Search Report, PCT/US03/031339, Feb. 18, 2004, 3 Pages.

International Search Report, PCT/US01/044977, Jun. 7, 2002, 6 Pages.

International Search Report and Written Opinion for International Application No. PCT/US2013/071144, mailed Mar. 6,2014, 10 pages.

European Search Report for European Application No. 13159256, Date Mailed: Oct. 17, 2013, 6 pages.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Avitall et al., "The creation of linear contiguous lesions in the atria with an expandable loop catheter," Journal of the American College of Cardiology, 1999; 33; pp. 972-984.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

ClinicalTrials.gov, Renal Denervation in Patients with uncontrolled Hypertension in Chinese (2011), 6pages. www.clinicaltrials.gov/ct2/show/NCT01390831.

(56) References Cited

OTHER PUBLICATIONS

Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.com/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards[TM]" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).

(56) References Cited

OTHER PUBLICATIONS

Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, Jan. 29, 2003, 23 pages.
Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*, 174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot$^{TM}$ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Stouffer, G. A. et al., Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium rentention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resis-

(56) References Cited

OTHER PUBLICATIONS tant Hypertension." Journal of the American College of Cardiology, 2013, doi: 10.1016/j.jacc.2013.07.046, 24 pages.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361;9.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimentla Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implictions for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
510K Summary of CryoGen Cryosurgery System, filed with FDA Jul. 3, 1997—approved Oct. 1, 1997, 1997, 5 pages.
CO2/Gas Composite Regulator, Sep. 6, 2011, 2 pages. <http://www.genuineinnovations.com/composite-regulator.html>.
CryoGen SS&E: HerOption Uterine Cryoblatin Therapy System, filed with FDA Aug. 15, 2000—approved Apr. 20, 2001,1999, 84 pages.
International Search Report and Written Opinion dated Apr. 12, 2012, International Application No. PCT/US2011/057514, 15 pages.
International Search Report and Written Opinion dated Apr. 13, 2012, International Application No. PCT/US2011/057502, 14 pages.
International Search Report and Written Opinion dated Dec. 28, 2011, International Application No. PCT/US2011/057508, 12 pages.
International Search Report and Written Opinion dated Feb. 14, 2012, International Application No. PCT/US2011/057504, 12 pages.
International Search Report and Written Opinion dated Feb. 20, 2012, International Application No. PCT/US2011/057483, 11 pages.
International Search Report and Written Opinion dated Feb. 23, 2012, International Application No. PCT/US2011/057490, 14 pages.
International Search Report and Written Opinion dated Feb. 6, 2012, International Application No. PCT/US2011/057497, 12 pages.
International Search Report and Written Opinion dated Jun. 13, 2013, International Application No. PCT/US2012/063411, 13 pages.
International Search Report and Written Opinion dated Mar. 16, 2012, International Application No. PCT/US2011/057511, 16 pages.
International Search Report and Written Opinion dated Mar. 9, 2012, International Application No. PCT/US2011/057523, 15 pages.
Lura Harrison, Ph.D. et al., "Cryosurgical Ablation of the A-V Node-His Bundle—A New Method for Producing A-V Block," Circulation, vol. 55, 1977 pp. 463-470.
Medical Grade Gas Dispenser, Sep. 6, 2011, 1 page, <http://www.abd-inc.com/Frame-904990-page1namepage904990.html?refresh=1205442262133>.
Sesia G. et al., "The use of nitrous oxide as a freezing agent in cryosurgery of the prostate," International Surgery [Int Surg], vol. 53, 1970, pp. 82-90.
Special Order Only Thermal Dilution Injector, Obsolete Product, Sep. 6, 2011, 1 page, <http://www.abd-inc.com/Frame-904990-page1namepage904990.html?refresh=1205442262133>.
Torre, Douglas, MD, "Alternate Cryogens for Cryosurgery," J. Derm. Surgery, Jun. 1975, pp. 56-58.
Voĭtyna SV, "Cryocatheter-tourniquet," Meditsinskaia Tekhnika [Med Tekh], vol. 6, 1976, pp. 47-48.
Claudine Jaboro, "An in vivo study of the biocompatibility of classic and novel device materials on the central nervous system", (Jan. 1, 2007), ETD Collection for Wayne State University. Paper AA13310737, 2 pages. <http://digitalcommons.wayne.edu/dissertations/AA13310737>.
European Search Report dated Jan. 30, 2013; European Application No. 12180426.4; Applicant: Medtronic Ardian Luxembourg S.a.r.l.; 6 pages.
European Search Report dated Feb. 28, 2013; European Application No. 12180427.2; Applicant: Medtronic Ardian Luxembourg S.a.r.l.; 4 pages.
European Search Report dated Jan. 30, 2013; Application No. 12180428.0; Applicant: Medtronic Ardian Luxembourg S.a.r.l.; 6 pages.
European Search Report dated Jan. 30, 2013; Application No. 12180430.6; Applicant: Medtronic Ardian Luxembourg S.a.r.l.; 6 pages.
European Search Report dated Jan. 30, 2013; Application No. 12180431.4; Applicant: Medtronic Ardian Luxembourg S.a.r.l.; 6 pages.
European Search Report dated Feb. 22, 2013; Application No. 12180432.2; Applicant: Medtronic Ardian Luxembourg S.a.r.l.; 6 pages.

(56) References Cited

OTHER PUBLICATIONS

International Search Report and Written Opinion dated Jan. 23, 2012, International Application No. PCT/US2011/057761, 13 pages.
International Search Report and Written Opinion dated Jan. 20, 2012, International Application No. PCT/US2011/057756, 10 pages.
International Search Report and Written Opinion dated Feb. 16, 2012, International Application No. PCT/US2011/057754, 13 pages.
Lahiri D. et al. "Boron nitride nanotube reinforced polylactide-polycaprolactone copolymer composite: Mechanical properties and cytocompatibility with osteoblasts and macrophages in vitro." Acta Biomater (2010), doi: 10.1016/j.actbio.2010.02.44, 10 pages.
Hanker et al., "Biomedical Materials and Devices," Materials Research Society Symposium Proceedings, vol. 110, Dec. 4, 1987, Boston Massachusetts, USA, 8 pages.

\* cited by examiner

CRYOTHERAPEUTIC DEVICES HAVING INTEGRAL MULTI-HELICAL BALLOONS AND METHODS OF MAKING THE SAME

TECHNICAL FIELD

The present technology relates generally to cryotherapeutic systems. In particular, several embodiments are directed to cryotherapeutic devices having integral multi-helical balloons and associated systems and methods.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine (NE) spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end-stage renal disease. In patients with end-stage renal disease, NE plasma levels above the median have been demonstrated to be predictive for cardiovascular diseases and several causes of death. This is also true for patients suffering from diabetic or contrast nephropathy. Evidence suggests that afferent signals originating from diseased kidneys are major contributors to initiating and sustaining elevated central sympathetic outflow.

Sympathetic nerves to the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Accordingly, there is a strong public-health need for alternative treatment strategies.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present technology. Furthermore, components can be shown as transparent in certain views for clarity of illustration only and not to indicate that the illustrated component is necessarily transparent.

DETAILED DESCRIPTION

Figure 1:
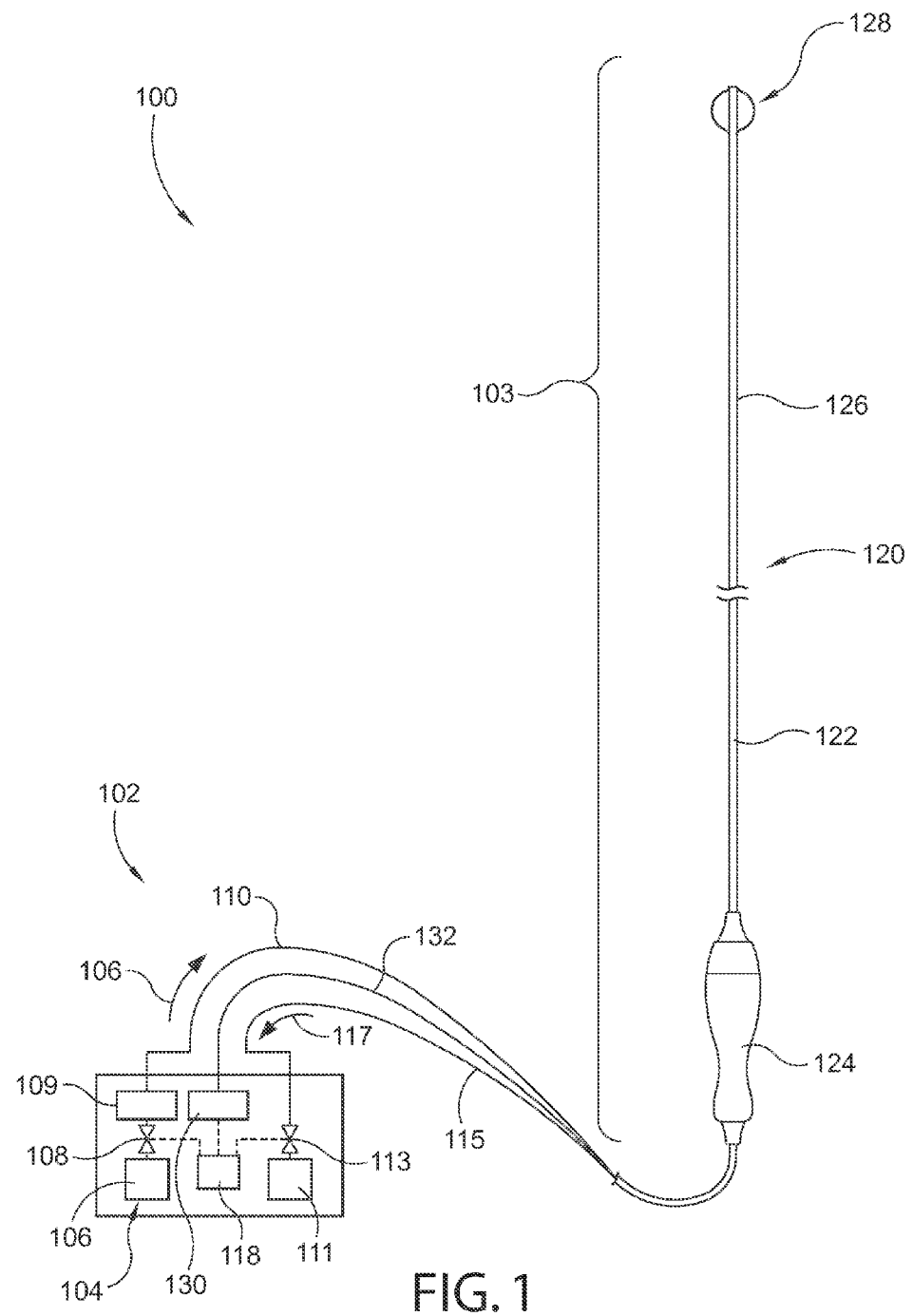
FIG. 1 is a partially schematic diagram illustrating a cryotherapeutic system configured in accordance with an embodiment of the present technology.

The present technology is directed to cryotherapeutic devices having integral multi-lumen shafts with multi-helical balloon sections and methods of making the devices. Specific details of several embodiments of the present technology are described herein with reference to FIGS. 1-11. Although many of the embodiments are described herein with respect to devices, systems, and methods for modulation of renal nerves using cryotherapeutic approaches, other applications and other embodiments in addition to those described herein are within the scope of the present technology. Additionally, several other embodiments of the present technology can have different configurations, components, or procedures than those described herein. A person of ordinary skill in the art, therefore, will understand that the present technology can have other embodiments with additional elements and features, or the present technology can have other embodiments without several of the elements and features described herein with reference to FIGS. 1-11.

The terms "distal" and "proximal" are used in the following description with respect to a position or direction relative to the operator or the operator's control device (e.g., a handle assembly). "Distal" or "distally" are a position distant from or in a direction away from the operator or the operator's control device. "Proximal" and "proximally" are a position near or in a direction toward the operator or the operator's control device.

I. Cryotherapy and Renal Neuromodulation

Cryotherapeutic systems and components of cryotherapeutic systems configured in accordance with embodiments of the present technology can be configured for renal neuromodulation, i.e., the partial or complete incapacitation or other effective disruption of nerves innervating the kidneys. In particular, renal neuromodulation can include inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation can contribute to the systemic reduction of sympathetic tone or drive. Accordingly, renal neuromodulation is expected to be useful in treating clinical conditions associated with systemic sympathetic overactivity or hyperactivity, particularly conditions associated with central sympathetic overstimulation. Renal neuromodulation is expected to efficaciously treat hypertension, heart failure, acute myocardial infarction, metabolic syndrome, insulin resistance, diabetes, left ventricular hypertrophy, chronic and end-stage renal disease, inappropriate fluid retention in heart failure, cardio-renal syndrome, polycystic kidney disease, polycystic ovary syndrome, osteoporosis, and sudden death, among others. Furthermore, renal neuromodulation can potentially benefit a variety of organs and bodily structures innervated by sympathetic nerves. A more detailed description of pertinent patient anatomy and physiology is provided below.

Various techniques can be used to partially or completely incapacitate neural pathways, such as those innervating the kidneys. Cryotherapy, for example, includes cooling tissue at a target site in a manner that modulates neural function. The mechanisms of cryotherapeutic tissue damage include, for example, direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Several embodiments of the present technology include cooling a structure at or near an inner surface of a renal artery wall such that proximate (e.g., adjacent) tissue is effectively cooled to a depth where sympathetic renal nerves reside. For example, the cooling structure can be cooled to the extent that it causes therapeutically effective cryogenic renal neuromodulation. Sufficiently cooling at least a portion of a sympathetic renal nerve is expected to slow or potentially block conduction of neural signals to produce a prolonged or permanent reduction in renal sympathetic activity.

Cryotherapy has certain characteristics that can be beneficial for renal neuromodulation. For example, rapidly cooling tissue can provide an analgesic effect such that cryotherapies may be less painful than ablating tissue at high temperatures. Cryotherapies may thus require less analgesic medication to maintain patient comfort during a procedure compared to heat-ablation procedures. Additionally, reducing pain can reduce patient movement and thereby increase operator success or reduce procedural complications. Cryotherapy also typically does not cause significant collagen tightening, and therefore is not typically associated with vessel stenosis. Cryotherapies generally include cooling at temperatures that cause cryotherapeutic applicators to adhere to moist tissue. This can be beneficial because it can promote stable, consistent, and continued contact during treatment. The typical conditions of treatment can make this an attractive feature because, for example, a patient can move during treatment, a catheter associated with an applicator can move, and/or respiration can cause the kidneys to rise and fall and thereby move the renal arteries. In addition, blood flow is pulsatile and causes the renal arteries to pulse. Adhesion associated with cryotherapeutic cooling also can be advantageous when treating short renal arteries in which stable intravascular positioning can be more difficult to achieve.

II. Selected Embodiments of Cryotherapeutic Systems

FIG. 1 is a partially schematic diagram illustrating a cryotherapeutic system 100 ("system 100") configured in accordance with an embodiment of the present technology. The system 100 can include a console 102 and a cryotherapeutic device 103. As shown in FIG. 1, the console 102 can include a supply container 104, a refrigerant 106 within the supply container 104, and a supply control valve 108 in fluid communication with the supply container 104. The supply container 104 can be, for example, a cartridge (e.g., a single-use cartridge) or a container that contains a sufficient volume of refrigerant 106 to perform multiple procedures (e.g., a canister, a refillable tank, a cylinder, or another suitable container that is not a cartridge). The supply container 104 can be configured to contain the refrigerant 106 at a desired pressure. For example, the supply container 104 can be configured to contain nitrous oxide ($N_2O$) at a pressure of about 750 psi or higher, which can allow the $N_2O$ to be in a liquid or substantially liquid phase at about ambient temperature. In other embodiments, the refrigerant 106 can include carbon dioxide ($CO_2$), hydrofluorocarbon (e.g., FREON made available by E. I. du Pont de Nemours and Company of Wilmington, Del.), and/or other suitable fluids that can be contained within the supply container 104 at a sufficiently high pressure to be in at least a substantially liquid phase at about ambient temperature. For example, R-410A, a zeotropic, but near-azeotropic mixture of difluoromethane ($CH_2F_2$; also known as HFC-32 or R-32) and pentafluoroethane ($CHF_2CF_3$; also known as HFC-125 or R-125), can be in at least a substantially liquid phase at about ambient temperature when contained at a pressure of about 210 psi. In some embodiments, the cryotherapeutic system 100 can be configured to pre-cool the refrigerant 106, and thereby increase the cooling potential of the refrigerant 106. A pre-cooler 109 can be part of the console 102 as shown in FIG. 1, integrated with the therapeutic device 103, and/or positioned elsewhere within the cryotherapeutic system 100.

The console 102 can include or be fluidly coupled to a supply line 110 configured to transport the refrigerant 106 to the cryotherapeutic device 103. The supply control valve 108 can be operably coupled to the supply line 110, and can be configured to manually or automatically control the flow of refrigerant 106 along the supply line 110. The console 102 can further include a pump 111 (e.g., a vacuum pump, a DC-powered pump, etc.), a back-pressure control valve 113, and an exhaust line 115. The exhaust line 115 can be configured to receive exhausted refrigerant 117 from the cryotherapeutic device 103, and the back-pressure control valve 113 can be operably coupled to the exhaust line 115. The pump 111 can be configured to reduce the back pressure of exhausted refrigerant 117 to below ambient pressure. Reducing the back pressure of exhausted refrigerant 117 to below ambient pressure using the pump 111 (e.g., in conjunction with increasing the flow rate of refrigerant 106 using the supply control valve 108) can increase the refrigeration potential of the refrigerant 106. In other embodiments, the exhausted refrigerant 117 can exhaust to about ambient pressure. In various embodiments, the console 102 can further include a controller 118 configured to operate the supply control valve 108 and/or the back-pressure control valve 113. The controller 118, for example, can include a processor (not shown) or dedicated circuitry (not shown) configured to implement a computerized algorithm for executing a treatment procedure or a portion of a treatment procedure automatically.

As shown in FIG. 1, the cryotherapeutic device 103 can include a shaft 120 having a proximal portion 122, a handle 124 at a proximal region of the proximal portion 122, and a distal portion 126 extending distally relative to the proximal portion 122. The cryotherapeutic device 103 can further include a cooling assembly 128 at the distal portion 126 of the shaft 120. As described in further detail below, the cooling assembly 128 can include an inflatable/deflatable body (e.g., a balloon) having a plurality of intertwined (e.g., twisted or curved, such as helical) lumens in which the refrigerant 106 expands or otherwise flows to provide cryogenic cooling. The shaft 120 can be configured to locate the distal portion 126 and/or the cooling assembly 128 intravascularly at a treatment site proximate (e.g., in or near) a renal artery or renal ostium, and the cooling assembly 128 can be configured to provide therapeutically effective cryogenic renal neuromodulation at the treatment site.

In various embodiments, the system 100 can be configured to monitor the pressure within a portion of the cryotherapeutic device 103 during a treatment procedure. As shown in FIG. 1, for example, the console 102 can include a pressure sensor 130 (e.g., a PX209-100G5V pressure transducer made by OMEGA Engineering Inc. of Stamford, Conn.) and a pressure line 132. The pressure sensor 130 can be operably coupled to the controller 118 and can be part of a feedback loop configured to control the supply control valve 108 and/or the back-pressure control valve 113. Flow of the refrigerant 106 to and/or from the cryotherapeutic device 103 can be regulated in response to a sensed pressure. For example, the pressure sensor 130 can be configured to indicate a pressure above a predetermined threshold value or range (e.g., a value or range at or below a burst pressure of an inflatable body of the cooling assembly 128). In response, the controller 118 can be configured to decrease or terminate flow of the refrigerant 106 to the cooling assembly 128 by at least partially closing the supply control valve 108. Similarly, the controller 118 can be configured to increase flow of the refrigerant 106 from the cooling assembly 128 by reducing the back pressure of the exhausted refrigerant 117 (e.g., by using the pump 111). In other embodiments, the pressure sensor 130 can be coupled directly to the supply control valve 108 and/or the back-pressure control valve 113 to automatically regulate the supply control valve 108 and/or the back-pressure control valve 113 in response to a sensed pressure.

Figure 2:
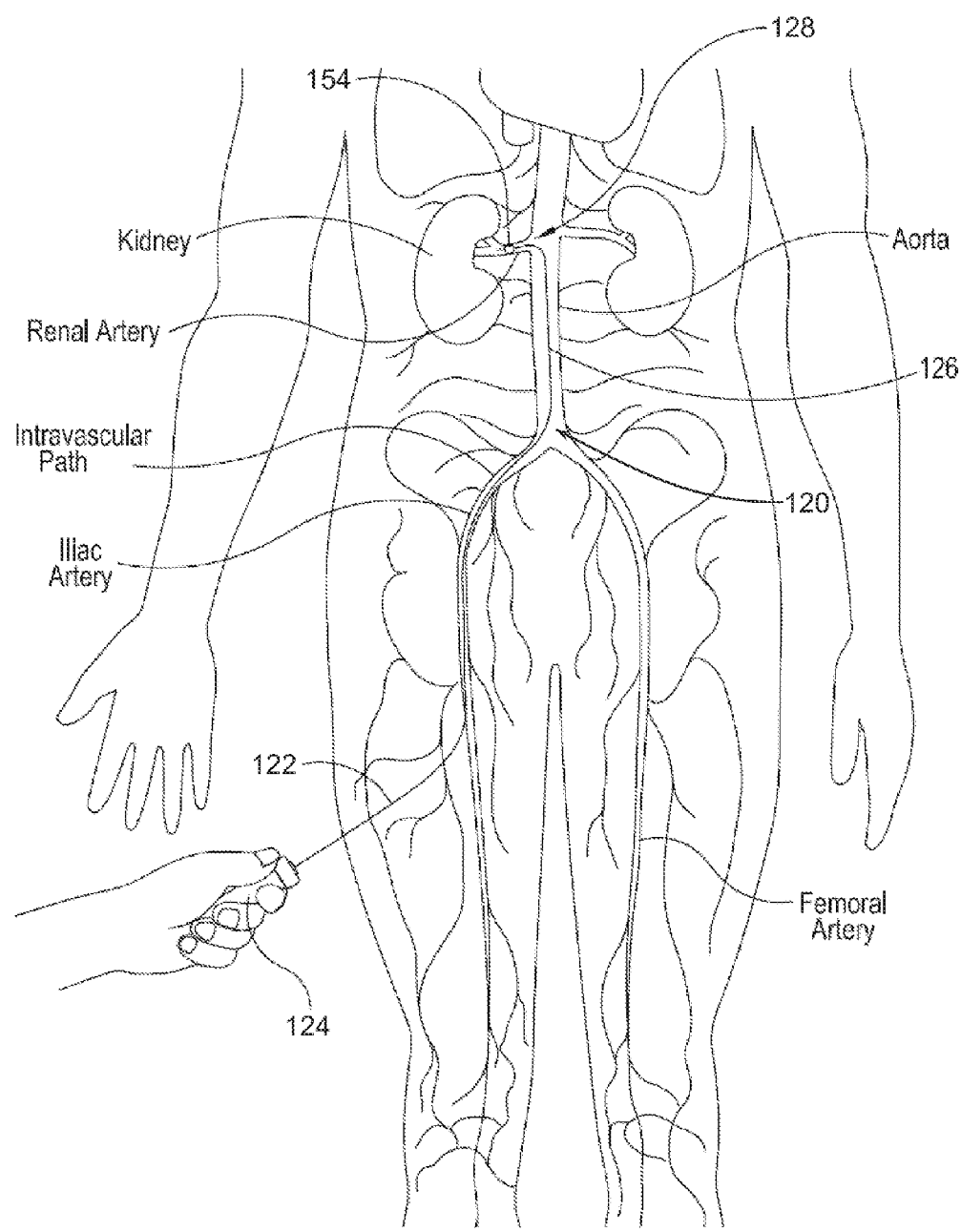
FIG. 2 is a diagram illustrating cryogenically modulating renal nerves in accordance with an embodiment of the present technology.

The system 100 may be used for neuromodulation at various target sites throughout the body. For example, FIG. 2 illustrates modulating renal nerves with an embodiment of the system 100 of FIG. 1. The cryotherapeutic device 103 can provide access to the renal plexus through an intravascular path, such as from a percutaneous access site in a femoral (FIG. 2), brachial, radial, axillary or other artery to a targeted treatment site within a respective renal artery. As illustrated, a section of the proximal portion 122 of the shaft 120 is exposed externally of the patient. By manipulating the proximal portion 122 of the shaft 120 from outside the intravascular path (e.g., via the handle 124), the operator may advance the shaft 120 through the sometimes tortuous intravascular path and remotely manipulate or actuate the distal portion 126 of the shaft 120. Image guidance, e.g., computed tomography (CT), fluoroscopy, intravascular ultrasound (IVUS), optical coherence tomography (OCT), or another suitable guidance modality, or combinations thereof, may be used to aid the operator's manipulation. Further, in some embodiments, image guidance components (e.g., IVUS, OCT) may be incorporated into the cryotherapeutic device 103 itself.

After the cooling assembly 128 is adequately positioned in the renal artery or at the renal ostium, it can be inflated or otherwise radially expanded at the target site until the cooling assembly 128 is positioned in stable contact with the inner wall of the renal artery. For example, the cooling assembly 128 can be inflated by delivering the refrigerant 106 (FIG. 1) or other cryogenic agent to at least a portion of the cooling assembly 128 (e.g., a lumen of an inflatable body) such that the refrigerant can expand from a liquid to a gas phase and thereby provide cooling to the inner wall of the renal artery. Other portions of the cooling assembly 128 (e.g., other lumens of the inflatable body) can be inflated with non-cryogenically cooled fluids (e.g., air, nitrogen, saline, etc.) or by the exhaust of the expanded refrigerant 106. The purposeful application of cooling from an applicator portion of the cooling assembly 128 is expected to induce one or more desired neuromodulating effects on localized regions of the renal artery and adjacent regions of the renal plexus, which lay intimately within, adjacent to, or in close proximity to the adventitia of the renal artery. The purposeful application of the cryogenic cooling may achieve neuromodulation along all or at least a portion of the renal plexus. In other embodiments, the cryotherapeutic device 103 may be intravenously introduced such that the cryotherapeutic device 103 can apply cryogenic cooling to denervate or otherwise modulate nerves proximate a renal vein. In further embodiments, the cryotherapeutic device 103 may be used for neuromodulation elsewhere in the body. For example, the cooling assembly 128 may be used in various cardiac applications to modulate abnormal electrical pathways for atrial fibrillation (AF), supraventricular tachycardia (SVT), atrial tachycardia, etc.

The neuromodulating effects are generally a function of, at least in part, the temperature of the cooling assembly 128, contact between the cooling assembly 128 and vessel wall, dwell time of the cooling assembly 128, number of cooling cycles (e.g., one or more cooling cycles separated by a warming period), and blood flow through the vessel. Desired cooling effects may include cooling the cooling assembly 128 such that the temperatures of target neural fibers are below a desired threshold to achieve cryo alteration or ablation. For example, the refrigerant gas in the cooling assembly 128 can be cooled to a temperature of about −88° C. to about −60° C., or in other embodiments the gas in the cooling assembly 128 can have a temperature of about −80° C. to about −40° C.

Therapeutically effective cryogenic renal neuromodulation can occur within about 100 seconds (e.g., within about 90 seconds, 75 seconds, 60 seconds, or 30 seconds) of the cooling assembly 128 reaching a cryogenic temperature when adjacent to the renal artery or renal ostium or of the cooling assembly 128 being applied to the renal artery or renal ostium when the cooling assembly 128 is already cryogenically cooled. In some embodiments, a treatment procedure can include two cooling cycles separated by a warming period. In other embodiments, a treatment procedure can include more than two cooling cycles separated by warming periods. The cooling cycles can have the same duration or different durations, such as between about 10 seconds and about 90 seconds each. The duration(s) of the warming periods can be sufficient to partially or completely thaw frozen matter at an interface between the cooling assembly 128 and the inner wall of the renal artery or renal ostium. In some embodiments, the duration(s) of the warming periods can be between about 5 seconds and about 90 seconds. Individual warming periods between cooling cycles can last for the same amount of time or for different amounts of time. In various embodiments, warming cycles may include deflating the cooling assembly 128 (e.g., by terminating the flow of refrigerant to the cooling assembly 128) to allow blood to flow around and warm the cooling assembly 128. The blood flow can partially or fully thaw frozen matter at the interface between the cooling assembly 128 and the arterial wall, and thereby detach the cooling assembly 128 from the tissue. Warming cycles may also include filling at least some of the lumens of the cooling assembly 128 with a warm fluid after a cooling cycle.

Figure 3A:
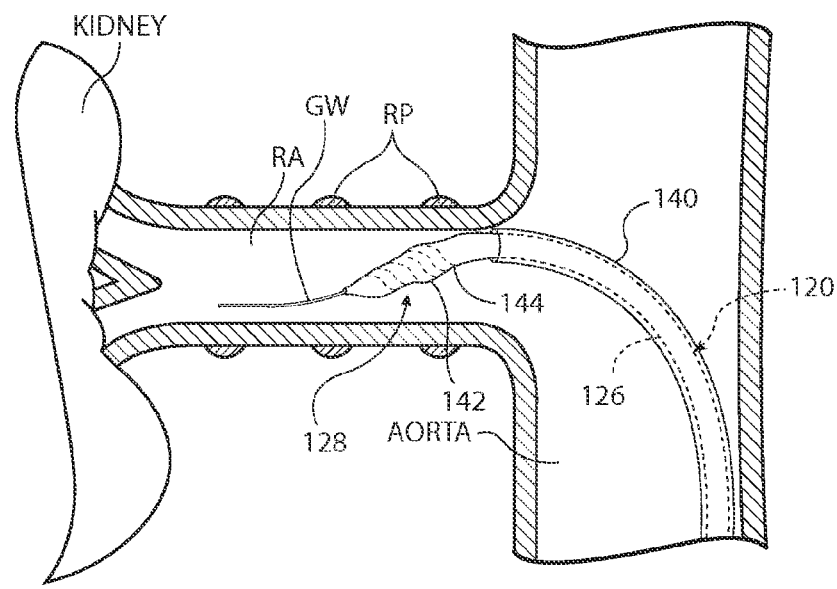
FIG. 3A is an enlarged side view of a distal portion of a cryotherapeutic device in a delivery state within a renal artery in accordance with an embodiment of the present technology.
Figure 3B:
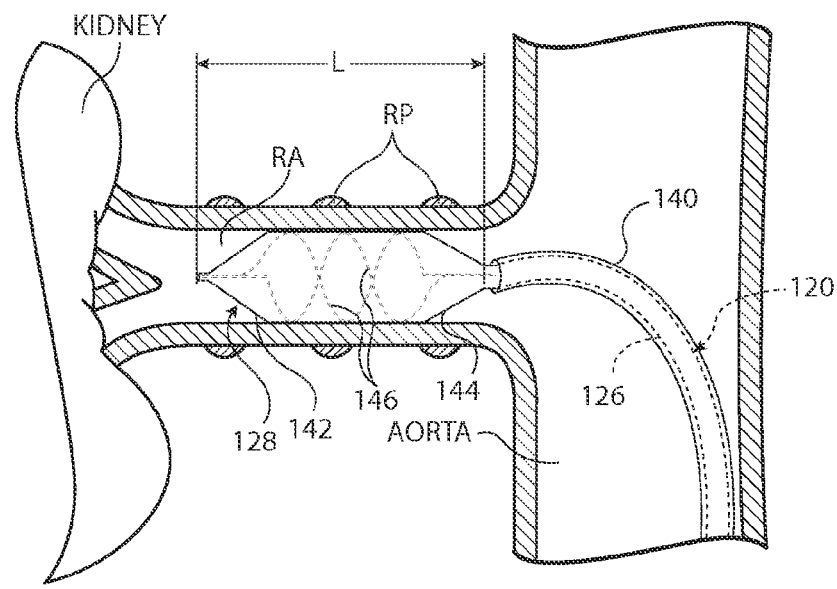
FIG. 3B is an enlarged side view of the distal portion of the cryotherapeutic device of FIG. 3A in a deployed state within the renal artery in accordance with an embodiment of the present technology.

FIGS. 3A and 3B are enlarged side views of the cooling assembly 128 of FIG. 1 in a delivery state (e.g., a low-profile or collapsed configuration) and a deployed state (e.g., an expanded configuration), respectively, within a renal artery RA in accordance with an embodiment of the present technology. The delivery state of the cooling assembly 128 can facilitate delivery (e.g., insertion) and/or removal of the cooling assembly 128 and, in certain embodiments, repositioning of the cooling assembly 128 at a treatment site. For example, in the embodiment illustrated in FIG. 3A, the cooling assembly 128 has a delivery state sized and shaped to navigate into and out of the renal artery RA. In other embodiments, the cooling assembly 128 can have other delivery configurations shaped and sized to fit within other portions of the vasculature and/or other structures within the body (e.g., larger delivery profiles for larger vessels and/or organs).

At least a portion of the cooling assembly 128 can be placed in a guide catheter or sheath 140 that flexes and/or otherwise facilitates navigation through the vasculature to locate the distal portion 126 of the shaft 120 proximate a treatment site, e.g., within the renal artery RA. For example, the guide catheter 140 may have a 6 Fr outer diameter with a lumen diameter of approximately 1.80 mm (0.071 inch). A guide wire GW can be used in addition to or in lieu of the guide catheter 140 to facilitate delivery of the cooling assembly 128 to the treatment site. The guide wire GW can be inserted through the vasculature to the treatment site, and the shaft 120 and/or the guide catheter 140 can be passed over the guide wire GW to the treatment site. At the treatment site, the guide catheter 140 and the shaft 120 can be moved relative to one another to expose the cooling assembly 128. For example, the guide catheter 140 can be pulled proximally or otherwise retracted from the distal end of the shaft 120, and/or the shaft 120 can be pushed distally from the opening of the guide catheter 140. In various embodiments, the cooling assembly 128 may deploy automatically (e.g., using a shape memory material) as it is exposed from the guide catheter 140. In other embodiments, the cooling assembly 128 can remain in a substantially low-profile configuration until the operator initiates deployment (e.g., via the handle 124 shown in FIGS. 1 and 2).

As shown in FIG. 3B, the cooling assembly 128 can include an inflatable body or region 142 (e.g., a balloon) that expands radially outward in the deployed state such that an outer wall 144 of the inflatable body 142 presses against or otherwise thermally contacts the inner surface of a vessel wall of the renal artery RA. For example, the inflatable body 142 can define at least a portion of an expansion chamber in which a refrigerant (e.g., the refrigerant 106 described above with reference to FIG. 1) expands or otherwise flows to provide cryogenic cooling and radial expansion of the inflatable body 142. As shown in FIG. 3B, in certain embodiments the inflatable body 142 can expand such that it at least partially occludes blood flow proximate the treatment site (e.g., in the renal artery RA). This configuration can reduce the variability of the neuromodulation procedures associated with blood flow.

The inflatable body 142 can include a plurality of inner walls 146 that extend from the outer wall 144 into the inflatable body 142 and divide the inflatable body 142 into a plurality of lumens. The inflatable body 142 may include, for example, two or more lumens (e.g., three, four, or five lumens) extending through the inflatable body 142. As shown in FIG. 3B, the inner walls 146 can be twisted along an axial length L of the inflatable body 142 such that the lumens form an intertwined helical or coiled pattern. The lumens are generally non-circumferential at longitudinal segments along the length L of the inflatable body 142. As described in further detail below, the multi-lumen inflatable body 142 can be a single extruded member and, in certain embodiments, may be formed integrally with the shaft 120 or a portion thereof (e.g., the distal portion 126). As such, the lumens may extend beyond the inflatable body 142 through at least a portion of the shaft 120.

In various embodiments, the lumens can be pressurized and/or inflated with fluids having different temperatures to provide selective cryotherapeutic treatment to arterial or venous walls. For example, a first lumen extending through the inflatable body 142 may define an expansion chamber and be configured to receive a cryogenically cooled fluid that provides therapeutically effective neuromodulation. A second lumen may be configured to receive a higher-temperature fluid that does not provide therapeutic neuromodulating effects. The second lumen may be configured to receive, for example, a heated fluid, a cooled fluid (e.g., a refrigerant) that is not at a therapeutically effective temperature, a gas at ambient temperature, a fluid at body temperature (e.g., blood), and/or other fluids at non-therapeutically effective temperatures. The differences in the fluid temperatures in the first and second lumens causes the inflatable body 142 to transfer heat to different areas of the inner wall of the renal artery RA at different rates, and the helical arrangement of the lumens results in different rates of heat transfer at longitudinal segments of the renal artery RA. The inflatable body 142 can therefore provide therapeutically effective cooling to non-circumferential longitudinal segments of the renal artery RA. In other embodiments, all of the lumens may be configured to receive cryogenically cooled fluids to provide fully circumferential neuromodulation at longitudinal segments of a vessel.

In various embodiments, the lumens of the inflatable body 142 can be fluidly isolated from one another. For example, the inflatable body 142 can include at least one cooling lumen fluidly coupled to a supply tube and an exhaust passageway.

The supply tube can deliver a refrigerant (e.g., nitrous oxide) in a liquid or substantially liquid state to the cooling lumen, and the refrigerant can expand to a gas state and therapeutically cool surrounding tissue. The exhaust passageway can be open to the cooling lumen and receive the refrigerant after expansion to remove the expanded refrigerant from the inflatable body 142. Other lumens of the inflatable body 142 can be fluidly coupled to separate supply and/or exhaust lumens and inflated with non-cryogenically cooled fluids. In other embodiments, the lumens of the inflatable body 142 can serve as the supply lumens for therapeutically cooled or non-therapeutically cooled fluids. As described in greater detail below, in other embodiments two or more of the lumens of the inflatable body 142 can be fluidly connected such that a refrigerant can be delivered to one lumen of the inflatable body 142 via a supply lumen and the expanded refrigerant can be exhausted proximally from the inflatable body 142 via a second lumen of the inflatable body 142.

In still further embodiments, different fluids and/or fluids having different temperatures can be supplied to the lumens of the inflatable body 142 during different time periods. For example, a refrigerant can be supplied to one or more lumens during a cooling cycle for partial or full-circumferential neuromodulation. The refrigerant supply can be slowed or terminated to begin a warming cycle, and a higher temperature fluid (e.g., warm saline) can be supplied in the same lumens and/or other lumens of the inflatable body 142 to warm the inflatable body 14 and transfer heat to the adjacent vessel wall. This can thaw frozen matter at the interface between the inflatable body 142 and the vessel wall, and thereby detach the inflatable body 142 from the vessel wall.

III. Methods of Forming Integral Multi-Helical Balloons

Figure 4A:
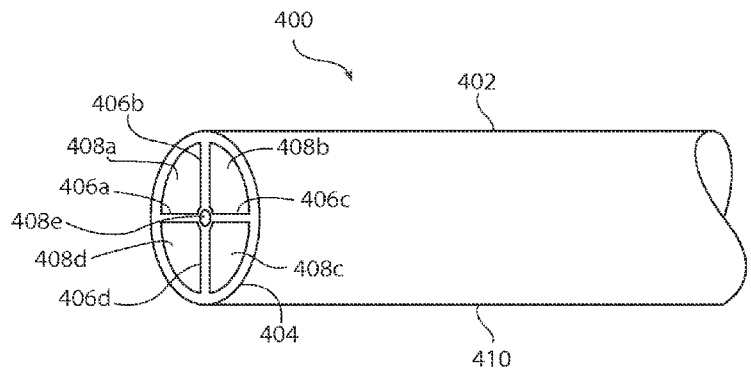
FIGS. 4A-4D are partially schematic isometric and side views illustrating a method of forming a distal portion of a cryotherapeutic device in accordance with an embodiment of the present technology.

FIGS. 4A-4D are partially schematic isometric and side views illustrating a method of forming a cooling assembly 400 of a cryotherapeutic device (e.g., the cryotherapeutic device 103 shown in FIG. 1) in accordance with an embodiment of the present technology. Referring to FIG. 4A, the method can include forming an elongated member or shaft 402 having an outer wall 404 formed integrally with one or more inner walls, webs or septums (individually identified as first through fourth inner walls 406a-d, respectively, and referred to collectively as inner walls 406). The outer and inner walls 404 and 406 can define a plurality of lumens (individually identified as first through fifth lumens 408a-e, respectively, and referred to collectively as lumens 408) extending along the shaft 402. In the embodiment illustrated in FIG. 4A, the shaft 402 includes four inner walls 406a-d that extend radially inward from the outer wall 404 to form the first through fourth lumens 408a-d extending at least substantially parallel and adjacent to one another (e.g., not coaxial) along the shaft 402. The outer lumens 408 can be defined by a portion of the outer wall 404 (e.g., a circular arc along a transverse cross-section of the shaft 402) and adjacent inner walls 406. The inner walls 406 may be spaced evenly about the circumference of the shaft 402 such that the outer lumens 408 have at least generally equal cross-sectional dimensions (e.g., cross-sectional areas). In other embodiments, the cross-sectional dimensions of the individual outer lumens 408 may differ. In further embodiments, the shaft 402 may include fewer than four outer lumens 408 (e.g., two or three lumens) or more than four outer lumens 408 (e.g., six, seven, or eight lumens).

As shown in FIG. 4A, the inner walls 406 can meet at a region (e.g., a central region) within the shaft 402 to form an inner lumen 408 (e.g., the fifth lumen 408e) positioned radially inward from the outer lumens 408 and extending at least substantially parallel to the outer lumens 408. The inner lumen 408e may be configured to receive a guide wire to facilitate delivery of the cooling assembly 400 to a treatment site (e.g., in a renal artery). In other embodiments, the shaft 402 may include additional inner lumens or the inner lumen 408e may be omitted.

The shaft 402 can be extruded such that the outer and inner walls 404 and 406 of the shaft 402 can be part of a single integrated component. For example, the shaft 402 can be formed from a thermoplastic resin using hot melt extrusion. In other embodiments, the shaft 402 can be formed by pushing or drawing a material (e.g., a polymeric material) through a die having a desired cross-sectional shape (e.g., the five-lumen shaft 402 illustrated in FIG. 4A). In certain embodiments, the extruded shaft 402 can have an outer boundary or surface 410 that is at least substantially continuous at longitudinal segments of the shaft 402, and the lumens 408 can be positioned within the continuous outer surface 410. As shown in FIG. 4A, for example, the outer surface 410 may have a continuous circular shape as seen in transverse cross-sections at various longitudinal locations along of the shaft 402. In other embodiments, the outer surface 410 of the shaft 402 may have other suitable cross-sectional shapes (e.g., rectangular, oval, irregular, etc.). In further embodiments, the shaft 402 can be integrally formed using other suitable methods known to those skilled in the art.

Figure 4B:
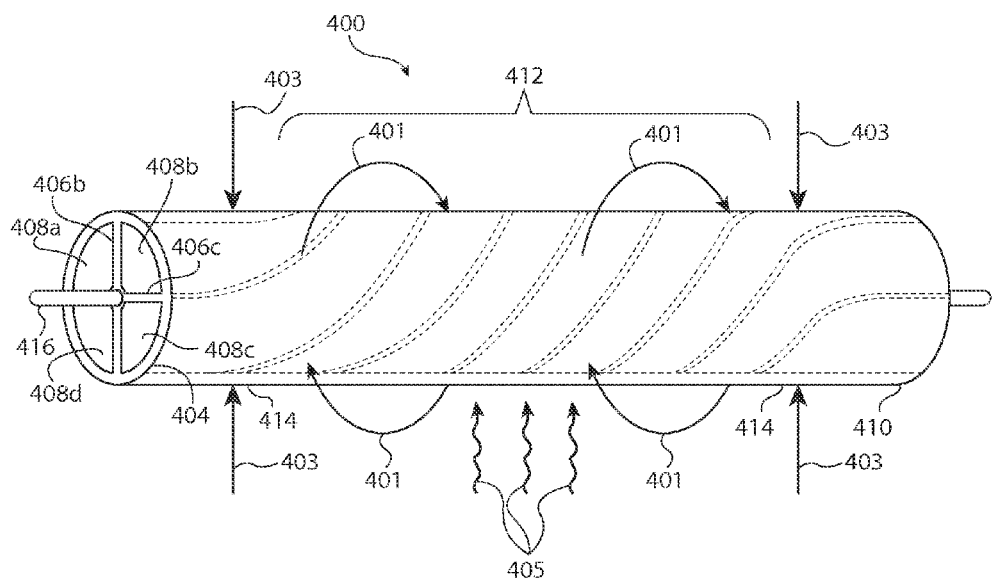

FIG. 4B illustrates another stage in the method of making the cooling assembly 400 that includes twisting (indicated by arrows 401) to a section 412 of the shaft 402. The section 412 can correspond to a longitudinal segment of the shaft 402 at which an inflatable body or balloon will subsequently be formed. In other embodiments, the section 412 can be longer or shorter than the subsequently-formed balloon, or may extend along a different section of the shaft 402. As shown in FIG. 4B, twisting the shaft 402 can include clamping (indicated by arrows 403) the shaft 402 at opposite end regions (identified individually as a proximal or first end region 414a and a distal or second end region 414b, and referred to collectively as ends regions 414) of the selected section 412 of the shaft 402, and applying twist 401 by rotating the clamps 403 in opposite directions with respect to one another. In other embodiments, the shaft 402 may be clamped only at the proximal end region 414a, and the shaft 402 can be twisted distal to the clamped proximal end region 414a. The clamp pressure can be applied circumferentially to the outer surface 410 of the shaft 402 (e.g., using an O-ring) to twist the section 412 of the shaft 402 without collapsing and/or permanently deforming the lumens 408. As such, the clamp pressure may depend on the amount of twist applied and the properties of the shaft (e.g., material, inner wall structures, etc.). Twisting the shaft 402 as shown in FIG. 4B can deform the inner walls 406 such that they are spiraled or curved along the section 412. The curved inner walls 406 can define twisted or helically shaped outer lumens 408 along the section 412. In certain embodiments, heat (indicated by arrows 405) can be applied to the shaft 402 or a portion thereof before and/or during twisting to facilitate twisting and/or otherwise deforming of the shaft 402.

As further shown in FIG. 4B, a mandrel 416 may be inserted through the inner lumen 408e to support the section 412 of the shaft 402 during formation of the cooling assembly 400. The interface between the section 412 and the mandrel 416 can have a relatively low frictional component to allow the section 412 to rotate and/or slide over the mandrel 416 during formation of the cooling assembly 400. An optional lubricant may be used at the shaft-to-mandrel interface to decrease the friction therebetween. The clamp pressure can be selected to ensure it does not bind the shaft 402 to the mandrel 416 during twisting. In various embodiments, the outer lumens 408 may also be supported by mandrels and/or other suitable inserts. The inserts for the outer lumens 408 should be sufficiently flexible and/or deformable (e.g., coiled spring inserts) to move and accommodate the twisting of the inner walls 406 without being crushed. In other embodiments, the lumens 408 can be pressurized to support the lumens 408 during clamping and twisting.

Figure 4C:
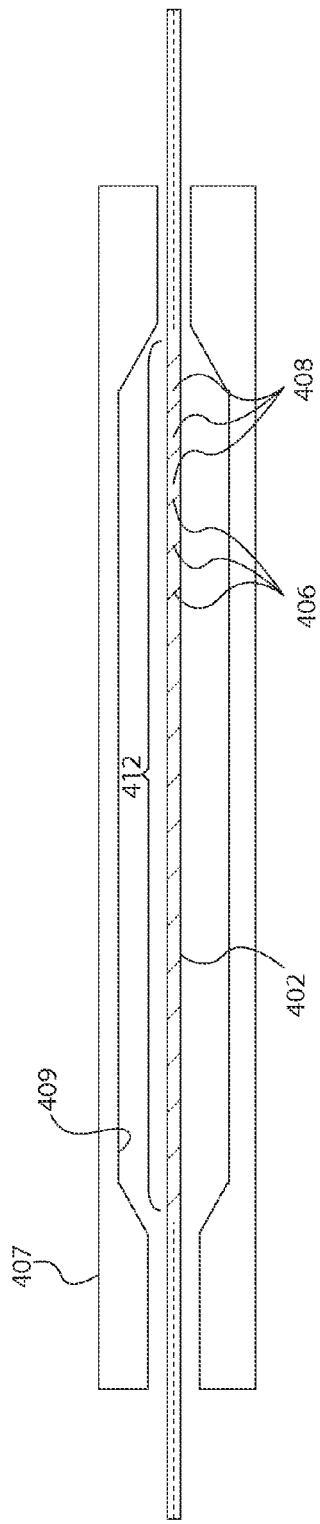
Figure 4D:
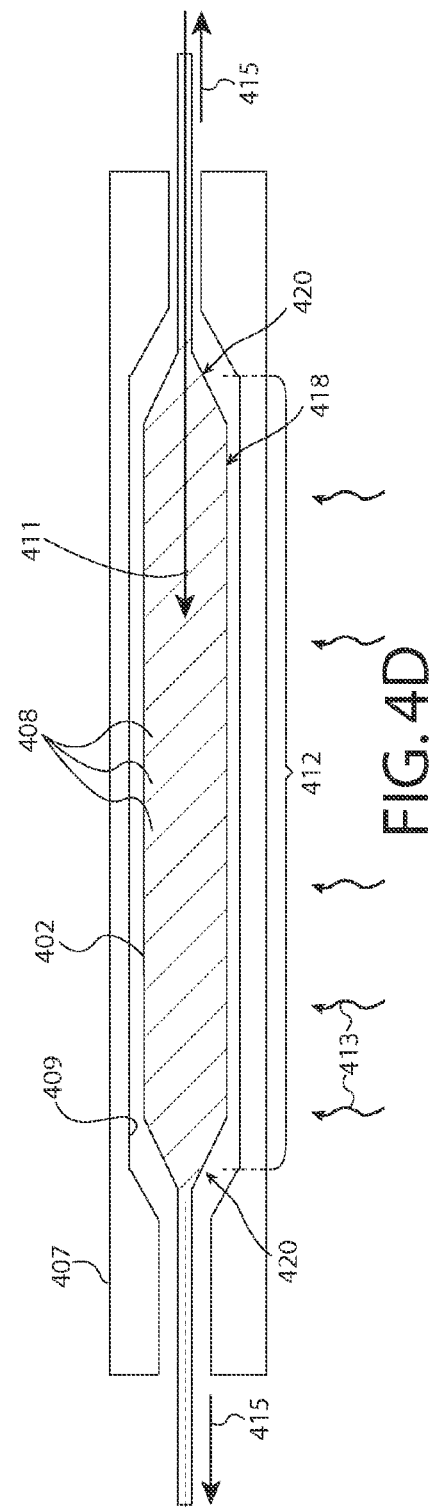

FIGS. 4C and 4D are schematic cross-sectional views illustrating the formation of an inflatable body or region 418 (FIG. 4D) along the shaft 402. As shown in FIG. 4C, a portion of the shaft 402 can be clamped or otherwise retained in a mold 407 having a recess or cavity 409 that defines an outer boundary of the inflatable body 418 to be formed. In embodiments where the inflatable body 418 is configured to fit within and/or occlude a renal artery, the cavity 409 can have a diameter of approximately 3-10 mm (0.118-0.394 inch) and a length of approximately 8-15 mm (0.315-0.591 inch). In other embodiments, the cavity 409 may be larger or smaller depending upon the target site.

As shown in FIG. 4C, the twisted section 412 of the shaft 402 (e.g., the portion with the intertwined helical lumens 408) or a portion thereof can be positioned in the cavity 409 and may define the preform or parison for subsequent blow molding. In the illustrated embodiment, the twisted section 412 extends the length of the cavity 409. In other embodiments, the twisted section 412 may be biased to one side of the cavity 409, and subsequent stretching and pressurization can lengthen the twisted section 412 such that it extends a desired length of the cavity 409. In further embodiments, the twisted section 412 can extend beyond the length of cavity 409 or be configured to extend along only a portion of the subsequently formed inflatable body 418.

As shown in FIG. 4D, air and/or another fluid can be delivered to (e.g., pumped into) a portion of the shaft 402 (as indicated by arrow 411) such that the increase in pressure within the shaft 402 plastically expands or enlarges the shaft 402 outward to conform to the shape of the mold cavity 409. The fluid can be delivered into the lumens 408 at least substantially equally across the cross-sectional area of the shaft 402 to provide substantially uniform radial expansion of the outer lumens 408. In other embodiments, the outer lumens 408 can be individually and/or selectively pressurized. The enlarged portion of the shaft 402 can define the inflatable body 418, which can be configured to deliver cryotherapeutic cooling at a treatment site.

As further shown in FIG. 4D, the shaft 402 may be put under tension (as indicated by arrows 415) before, during, and/or after pressurization. For example, a longitudinal force can be applied during pressurization to extend the length of the twisted section 412 to that of the cavity 409 and/or other desired lengths. A secondary stretching step can be applied after formation of the inflatable body 418 to decrease the thickness of the walls of the shaft 402 at neck portions 420 (opposing end portions) of the inflatable body 418. In various embodiments, thermoforming may also be used to form the inflatable body 418 whereby the shaft 402 may be heated (as indicated by arrows 413) during stretching and/or pressurization to facilitate lengthening and/or radial expantion the shaft 402. For example, the shaft 402 can be annealed at temperatures of about 65.6-148.9° C. (150-300° F.) during pressurization and stretching. In other embodiments, the inflatable body 418 can go through a secondary annealing step after formation (e.g., at about 75° C. (167° F.) for about 60 minutes).

Figure 4E:
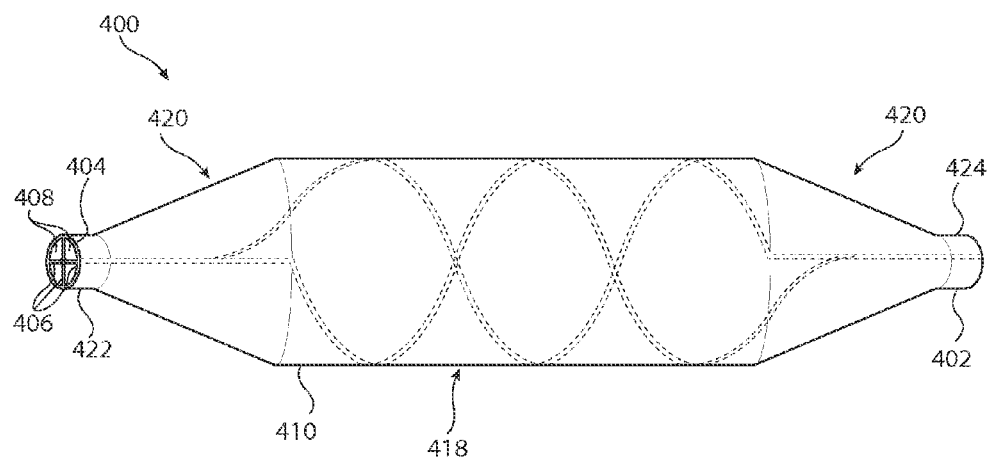
FIGS. 4E and 4F are isometric and cross-sectional isometric views, respectively, of the distal portion of the cryotherapeutic device formed using the method illustrated in FIGS. 4A-4D and configured in accordance with an embodiment of the present technology.
Figure 4F:
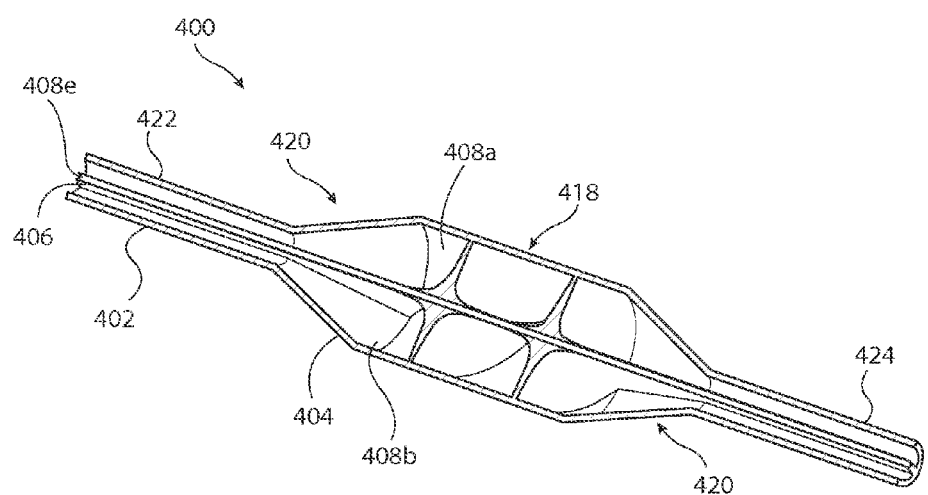

FIGS. 4E and 4F are enlarged isometric and cross-sectional isometric views, respectively, of the shaft 402 after the inflatable body 418 has been formed. The inflatable body 418 can be located at a distal portion of a cryotherapeutic device (e.g., the cryotherapeutic device 103 shown in FIG. 1) and configured to provide cryotherapeutic cooling (e.g., for neuromodulation) at a treatment site. In certain embodiments, the shaft 402 can include an elongated proximal portion 422 that extends proximally from the inflatable body 418 to a handle or controller (not shown; e.g., the handle 124 of FIG. 1) such that the proximal portion 422 defines a catheter shaft of the cryotherapeutic device. In other embodiments, the proximal portion 422 of the shaft 402 may extend a shorter distance from the inflatable body 418 (e.g., as shown in FIG. 4E) where it can be fluidly coupled to a separate catheter shaft (e.g., the shaft 120 of the cryotherapeutic device 103 of FIG. 1). In further embodiments, the shaft 402 can include an elongated distal portion 424 that extends distally beyond the inflatable body 418 and, optionally, attach to an end feature, such as an atraumatic tip or an end cap. In still further embodiments, the shaft 402 can terminate at the distal end of the inflatable body 418.

The inflatable body 418 can be configured to move between a delivery state (e.g., a collapsed, deflated, or low-profile configuration) and an inflated or deployed state (FIGS. 4E and 4F) in which the inflatable body 418 can deliver cryotherapeutic neuromodulation to a treatment site. In the deployed state, the outer lumens 408 of the inflatable body 418 can define separate fluid passageways that include intertwined helical portions along at least a portion of the inflatable body 418.

Figure 4G:
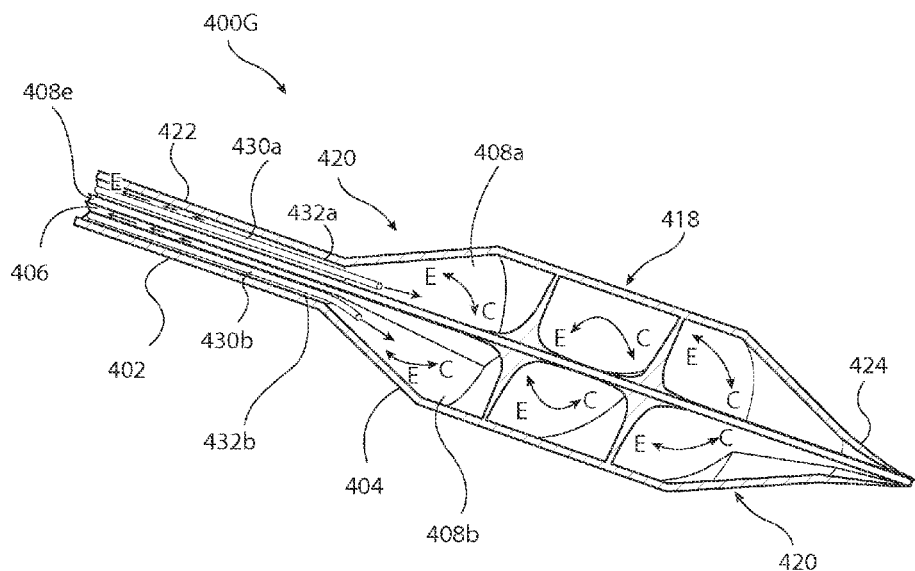
FIGS. 4G-4I are cross-sectional isometric views of cooling assemblies for cryotherapeutic devices configured in accordance with embodiments of the present technology.

In various embodiments, the lumens 408 can be fluidly independent of one another and configured to receive different types of fluids and/or fluids having different temperatures. FIG. 4G, for example, illustrates an embodiment of a cooling assembly 400G in which the first lumen 408a and the second lumen 408b are fluidly isolated from each another. As shown in FIG. 4G, the first lumen 408a can be fluidly coupled to a first supply tube or lumen 430a, and the second lumen 408b can be fluidly coupled to a second supply tube or lumen 430b (collectively referred to as supply tubes 430). The supply tubes 430 can be coupled to separate fluid sources (e.g., a supply of refrigerant, air, saline, etc.) at their proximal ends and deliver fluid to the corresponding lumens 408 from their distal ends. In other embodiments, the first and second supply tubes 430a and 430b can be coupled to the same fluid source. Fluids can flow distally from the supply tubes 430 along the individual lumens 408 (e.g., as indicated by the arrows C) to inflate the lumens 408, and move proximally through the same lumens (e.g., as indicated by the arrows E) to exhaust from the inflatable body 418 into the corresponding first and second exhaust passageways or lumens 432a and 432b (referred to collectively as exhaust passageways 432). The exhaust passageways 432 can be defined by the proximal portions 422 of the first and second lumens 408a and 408b as shown in FIG. 4G, or by a separate passageway. In certain embodiments, the first supply tube 430a can deliver a refrigerant (e.g., nitrous oxide) in a liquid or substantially liquid state to the first lumen 408a such that the refrigerant expands to a gas state in the first lumen 408a, and thereby inflates and cools the first lumen 408a to therapeutically effective neuromodulating temperatures. The second supply tube 430b can deliver fluids (e.g., air, saline, etc.) at non-therapeutically effective temperatures to the second lumen 408b to inflate the second lumen 408 and expand the inflatable body 418 into contact with a vessel wall. In other embodiments, the second lumen 408b can define the supply lumen. Cryogenically cooled fluids and/or non-cryogenically fluids can also be delivered via separate supply tubes to other lumens 408. Since the cryogenically cooled fluid is not supplied to all of the outer lumens 408, the inflatable body 418 can deliver therapeutically effective cooling to non-circumferential longitudinal segments of a vessel (e.g., the renal artery). In certain embodiments, the fluids selected for each lumen 408 can differ to accommodate a desired neuromodulation pattern. Accordingly, the inflatable body 418 can selectively apply therapeutically effective cooling to a treatment site based on the configuration of the lumens 408 and the fluids received therein.

Figure 4H:
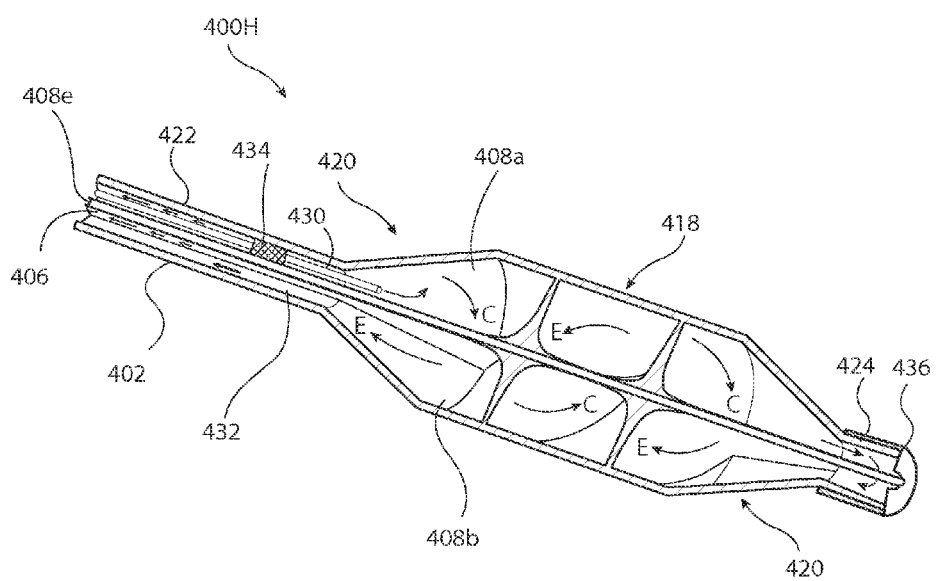

In other embodiments, two or more of the lumens 408 can be fluidly coupled to one another. FIG. 4H, for example, illustrates an embodiment of a cooling assembly 400H in which the first and second lumens 408a and 408b are fluidly coupled to each other via an end cap or nose feature 436 at the distal portion 424 of the inflatable body 418. As shown in FIG. 4H, the cooling assembly 400H can include one supply tube 430 that delivers a refrigerant (e.g., nitrous oxide) in a liquid or substantially liquid state to the first lumen 408a. The refrigerant expands to a gas state as it exits the supply tube 430 and then moves distally through the inflatable body 418 along the first lumen 408a (as indicated by the arrows C) to provide therapeutically effective cooling to an adjacent vessel wall. A bond or seal 434 can be positioned along the first lumen 408a proximal to the inflatable body 418 (e.g., around the supply tube 430) to prevent fluid (e.g., the refrigerant) from moving proximally through the first lumen 408a along the shaft 402. At the distal portion 424 of the inflatable body 418, the end cap 436 can fluidly couple the first lumen 408a to the second lumen 408b to allow the expanded refrigerant in the first lumen 408a to flow proximally through the inflatable body 418 along the second lumen 408b (as indicated by arrows E) and exit the inflatable body 418 via the exhaust passageway 432. The exhaust passageway 432 can be defined by the proximal portion 422 of the second lumen 408b and, optionally, a portion of the first lumen 408a proximal to the seal 434. In this embodiment, the expanded refrigerant in the second lumen 408b has already undergone the liquid-to-gas phase change (i.e., while in the first lumen 408a), and is therefore substantially warmer than the refrigerant in the first lumen 408b still undergoing the phase change. As such, the expanded refrigerant provides little to no therapeutic cooling effect along the second lumen 408b. Accordingly, the cooling assembly 400H shown in FIG. 4H can use refrigerant to inflate both the therapeutically cooled first lumen 408a and the non-therapeutically cooled second lumen 408b.

Figure 4I:
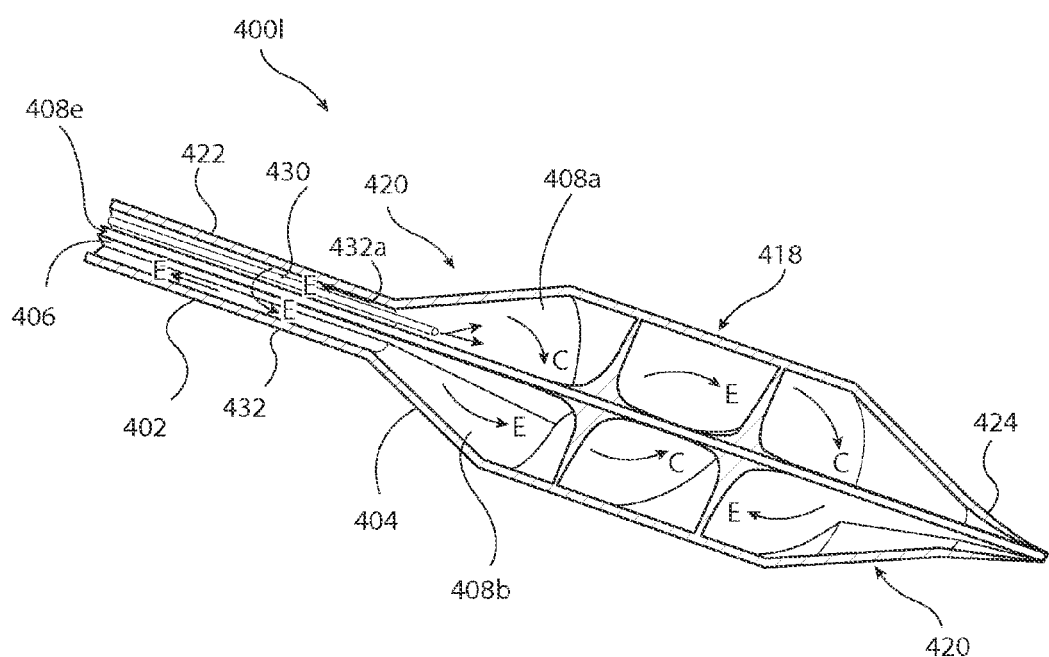

FIG. 4I illustrates another embodiment of a cooling assembly 400I in which the first and second lumens 408a and 408b are fluidly coupled to each other. In the embodiment illustrated in FIG. 4I, however, the first and second lumens 408a and 408b are fluidly coupled to each other proximal to the inflatable body 418. In operation, a refrigerant can be delivered to the first lumen 408a via the supply tube 430, and can expand within the first lumen 408a at the inflatable body 418 to provide a therapeutically cooled treatment region. After expansion, the refrigerant flows proximally along the first lumen 408a to the proximal portion 422 of the shaft 402 where the first and second lumens 408a and 408b are in fluid communication with one another. This configuration allows the expanded refrigerant to flow distally into and inflate the second lumen 408b (as indicated by arrows E) of the inflatable body 418. Therefore, the cooling assembly shown in FIG. 4A allows a refrigerant to be supplied to one lumens 408 for therapeutic cooling, and directs the expanded refrigerant into another lumen 408 in which it would have little to no therapeutic cooling effect Referring back to FIGS. 4E and 4F, the outer lumens 408 are multi-helical along the inflatable body 418 and at least substantially straight proximal and/or distal to the inflatable body 418. The neck portions 420 can optionally be used to gradually transition the outer lumens 408 from the multi-helical pattern at the inflatable body 418 to the straight path along the shaft 402. This configuration allows fluids to flow from supply lines (not shown; e.g., the supply line 110 of FIG. 1) along a more direct trajectory (e.g., a shorter trajectory) to the inflatable body 418 than if the lumens 408 were arranged in a helical or curved pattern proximally and/or distally of the inflatable body 418. This shorter flow path can reduce the total dwell time of the fluid in the proximal portion 422 of the shaft 402. The shorter flow path can also decrease the dwell time of the fluid in the lumens 408. This reduces the amount of time the fluid is exposed to internal body heat before being delivered to the inflatable body 418, and therefore allows the fluid to be introduced into the shaft 402 at a higher temperature, and reduces the extent of pre-cooling of the fluid (e.g., outside the body before entering the shaft 402 and/or within the body along the length of the shaft 402). In addition, the substantially straight fluid passageways formed by the lumens 408 proximal to the inflatable body 418 can facilitate fluid connections to other components (e.g., another shaft) in the cooling assembly 400 because fluid connections need not be made with the curved inner walls 406. In other embodiments, the helical portions of the lumens 408 can extend proximally and/or distally from the inflatable body 418.

As further shown in FIGS. 4E and 4F, the shaft 402 (including the inflatable body 418) can be part of a single integral extrusion that has a substantially continuous outer surface 410 along the length of the shaft 402 and/or at longitudinal cross-sectional segments of the shaft 402 (e.g., unlike conventional devices that include discrete balloons twisted around one another to form a helical lumens). When the inflatable body 418 is in the deployed state, the outer surface 410 can press against an adjacent inner wall of a vessel (e.g., the renal artery). The continuous outer surface 410, for example, can contact a vessel wall around a full circumference of the vessel wall. This can increase the available surface area with which the inflatable body 418 can contact the vessel wall (e.g., as compared to multiple balloon devices that may have gaps between the individual balloons) and may provide uniform contact with the vessel wall to enhance heat transfer at the target site.

Figure 5A:
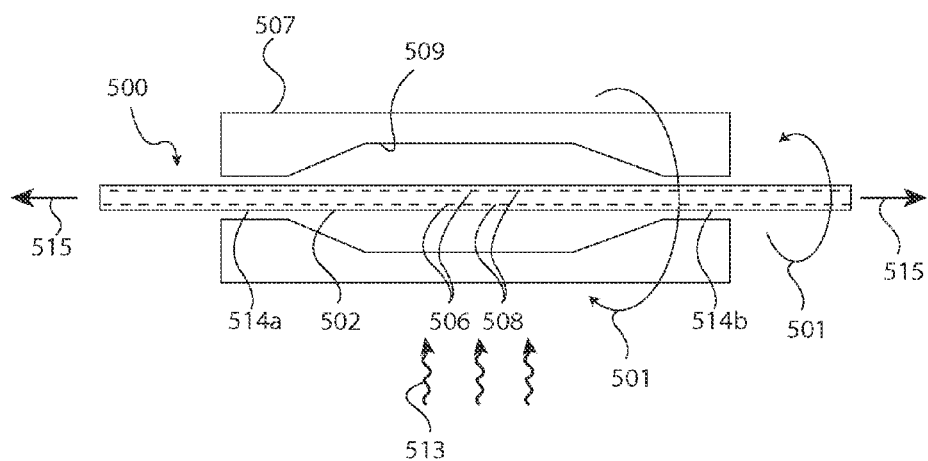
FIGS. 5A and 5B are partially schematic side views illustrating a method of forming a distal portion of a cryotherapeutic device in accordance with another embodiment of the present technology.
Figure 5B:
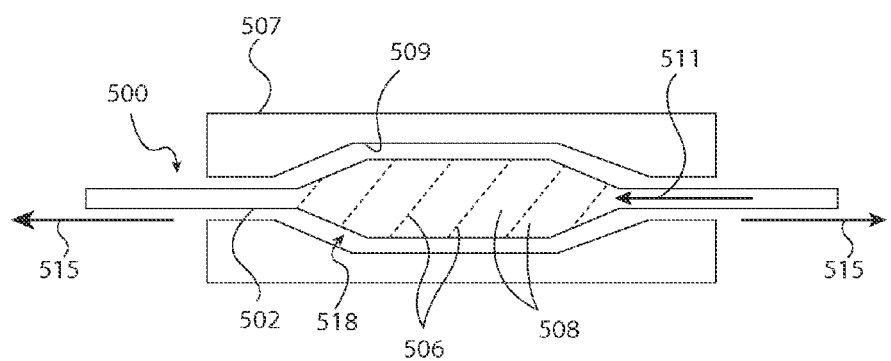

FIGS. 5A and 5B are partially schematic side views illustrating a method of forming a cooling assembly 500 in accordance with another embodiment of the present technology. The method can include steps generally similar to those of the method described above with respect to FIGS. 4A-4F. For example, the method can include extruding a multi-lumen shaft 502 from a material (e.g., a polymeric material). The shaft 502 can include a plurality of lumens 508 extending at least substantially parallel to one another along the shaft 502. As shown in FIG. 5A, a section of the shaft 502 can be positioned in a cavity 509 of a mold 507 that is configured to define an outer boundary of a subsequently formed inflatable region 518 (FIG. 5B) of the shaft 502.

As shown in FIG. 5A, twisting (indicated by arrows 501) can be applied to the shaft 502 while it is in the mold 507 by rotating the mold 507 and/or the shaft 502 relative to one another. For example, a proximal region 514a of the shaft 502 can be clamped by the mold 507 and a distal region 514b of the shaft 502 can be rotated to twist the section of the shaft 502 between the proximal and distal regions 514a and 514b. In other embodiments, the mold 507 itself can be rotated with respect to the shaft 502 and/or the shaft 502 can be rotated in opposing directions at the proximal and distal regions 514a and 514b. In various embodiments, the lumens 508 may be pressurized for support (e.g., to keep the lumens 508 open) as the shaft 502 is twisted. As further shown in FIG. 5A, the shaft 502 can be stretched (as indicated by arrows 515) and/or heated (as indicated by arrows 513) during twisting.

As shown in FIG. 5B, twisting the shaft 502 can form twisted or helical portions along the individual lumens 508. The helical portions of the lumens 508 can be plastically enlarged by stretch blow molding (e.g., pressure indicated by arrow 511 and tension indicated by arrows 515) and/or otherwise enlarging the shaft 502 to form a multi-helical inflatable region 518. Heat may be applied to the mold 507 or the shaft 502 while the inflatable region 518 is formed. In various embodiments, the helical portions of the lumens 508 and the inflatable region 518 can be formed in one step by simultaneously twisting and stretch blow molding the distal portion of the shaft 502. The inflatable region 518 can be positioned at a distal portion of a cryotherapeutic device and may be configured to selectively provide cryotherapeutic neuromodulation.

A method of forming a distal portion of a cryotherapeutic device (e.g., the cooling assembly 128 of the cryotherapeutic device 103 described above with reference to FIGS. 1-3B) in accordance with an embodiment of the present technology is also disclosed herein. The method can include extruding an integral multi-lumen shaft from a material. The shaft can be formed from, for example, a thermoplastic resin using a hot melt extrusion process. In other embodiments, the integral multi-lumen shaft can be formed using other suitable extrusion methods and/or from other suitable materials. The extruded shaft can include a plurality of outer lumens extending parallel to one another along a length of the shaft (e.g., the outer lumens 408a-c shown in FIGS. 4A-4F), and an optional guide wire lumen extending centrally between the outer lumens.

After the shaft has been formed, the method can continue by clamping opposite end regions of a portion of the shaft, and twisting at least one of the clamped end regions to form intertwined helical lumens along the portion. The shaft can be clamped using O-rings and/or other suitable clamping mechanisms, and the clamping force applied to the shaft can be sufficient to grasp the shaft while maintaining the integrity of the lumens. In various embodiments, mandrels can be extended through at least a portion of the lumens to keep the lumens open during the twisting step. For example, mandrels can be extended into the individual lumens at the end regions (e.g., at the clamp) to support the lumens as the clamping force is applied. In other embodiments, the lumens can be pressurized to support the lumens during the twisting step. In certain embodiments, the method can also include applying heat to the shaft during twisting. The heated shaft material can be more malleable, and therefore easier to shape into the intertwined helical lumens. The resultant shaft includes a twisted portion in which the lumens are intertwined. The lumens can extend substantially straight along the shaft proximal and/or distal to the twisted portion (e.g., outside of the clamped portion).

The method can further include plastically enlarging the twisted portion of the shaft to form an inflatable body. The shaft can be plastically enlarged using stretch blow molding techniques. For example, the twisted portion of the shaft can define a preform or parison that is placed into a cavity of a mold, pressurized, and stretched to enlarge or expand the shaft to form the inflatable body (e.g., a balloon). The mold cavity can have a shape corresponding to that of the desired inflatable body in an expanded or inflated state. In various embodiments, the shaft can be pressurized by delivering a fluid into the outer lumens through an end of the shaft (e.g., the distal end), and the resultant pressure increase within the lumens can expand or enlarge the portion of the shaft within the mold cavity. The fluid can be delivered into the lumens at least substantially equally across the cross-sectional area of the shaft to provide substantially uniform radial expansion of the outer lumens. The shaft can be stretched during the blow molding step to elongate the preform (e.g., the twisted portion of the shaft), and heat can be applied to facilitate stretching and/or blow molding. The enlarged portion of the shaft can define a balloon that can be configured to deliver cryotherapeutic cooling at a treatment site. The balloon can be attached to a distal end of a catheter shaft (e.g., the shaft 120 of FIG. 1) as part of a cooling assembly (e.g., the cooling assembly 128 of FIG. 1) and incorporated into a cryotherapeutic device. In other embodiments, the portion of the shaft proximal to the inflatable body can define the shaft of the cryotherapeutic device, and can be attached at a proximal end to a handle and/or console (e.g., the handle 124 and console 102 of FIG. 1).

IV. Related Anatomy and Physiology

The sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the SNS operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release norepinephrine. Prolonged activation may elicit the release of adrenaline from the adrenal medulla. Once released, norepinephrine binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The SNS is responsible for up and down regulation of many homeostatic mechanisms in living organisms. Fibers from the SNS innervate tissues in almost every organ system, providing at least some regulatory function to physiological features as diverse as pupil diameter, gut motility, and urinary output. This response is also known as the sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the SNS and indirectly via catecholamines secreted from the adrenal medulla.

Science typically looks at the SNS as an automatic regulation system, that is, one that operates without the intervention of conscious thought. Some evolutionary theorists suggest that the SNS operated in early organisms to maintain survival as the SNS is responsible for priming the body for action. One example of this priming is in the moments before waking, in which sympathetic outflow spontaneously increases in preparation for action.

A. The Sympathetic Chain

Figure 6:
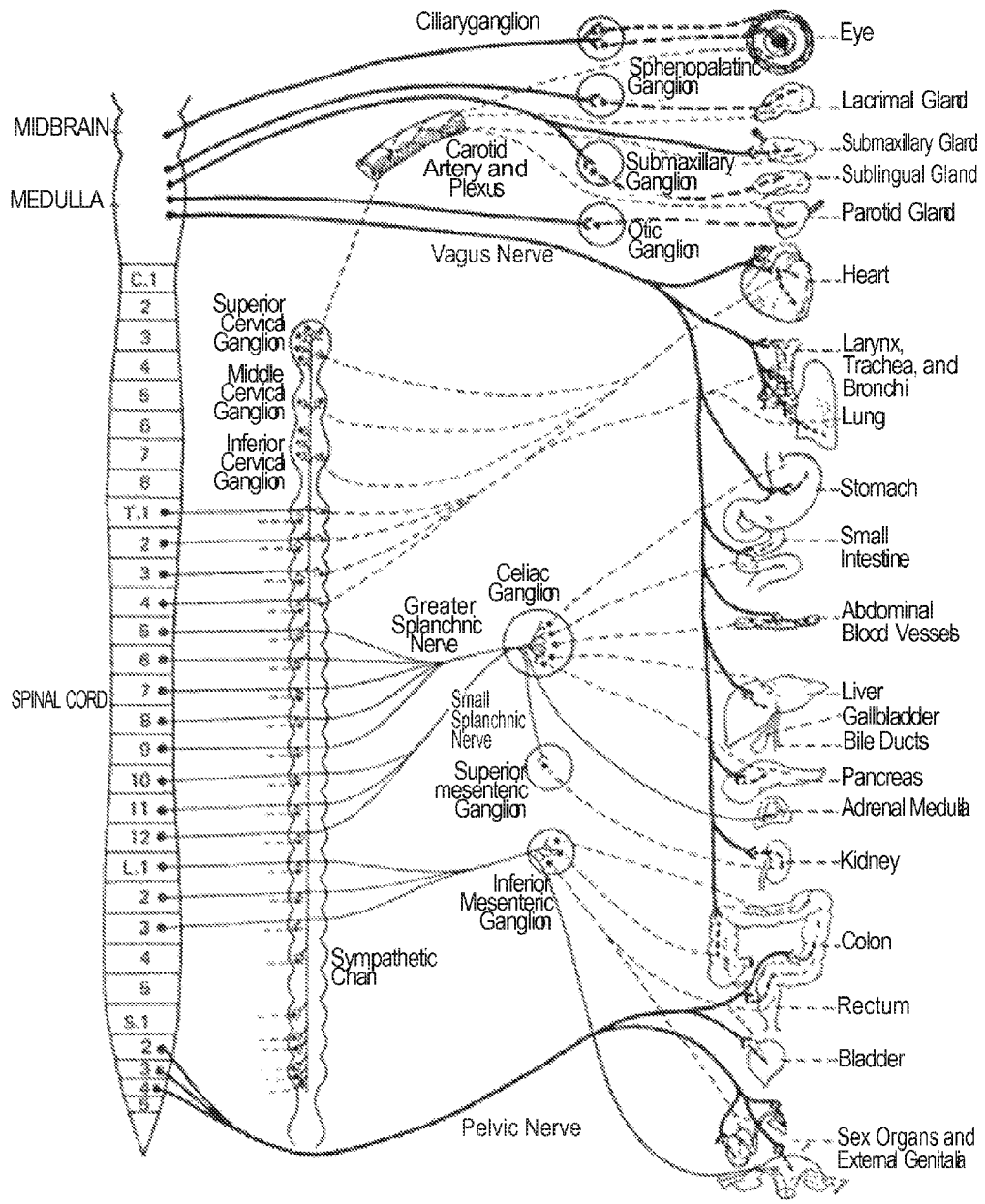
FIG. 6 is a conceptual diagram illustrating the sympathetic nervous system and how the brain communicates with the body via the sympathetic nervous system.

As shown in FIG. 6, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors that connect to either the paravertebral (which lie near the vertebral column) or prevertebral (which lie near the aortic bifurcation) ganglia extending alongside the spinal column.

In order to reach the target organs and glands, the axons travel long distances in the body. Many axon cells relay their messages to second cells through synaptic transmission. For example, the ends of axon cells can link across a space (i.e., a synapse) to dendrites of the second cell. The first cell (the presynaptic cell) can send a neurotransmitter across the synaptic cleft where it activates the second cell (the postsynaptic cell). The message is then carried to the final destination. In the SNS and other components of the PNS, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands. The ganglia include not just the sympathetic trunks but also the cervical ganglia (superior, middle, and inferior), which send sympathetic nerve fibers to the head and thorax organs, and the celiac and mesenteric ganglia, which send sympathetic fibers to the gut.

B. Innervation of the Kidneys

Figure 7:
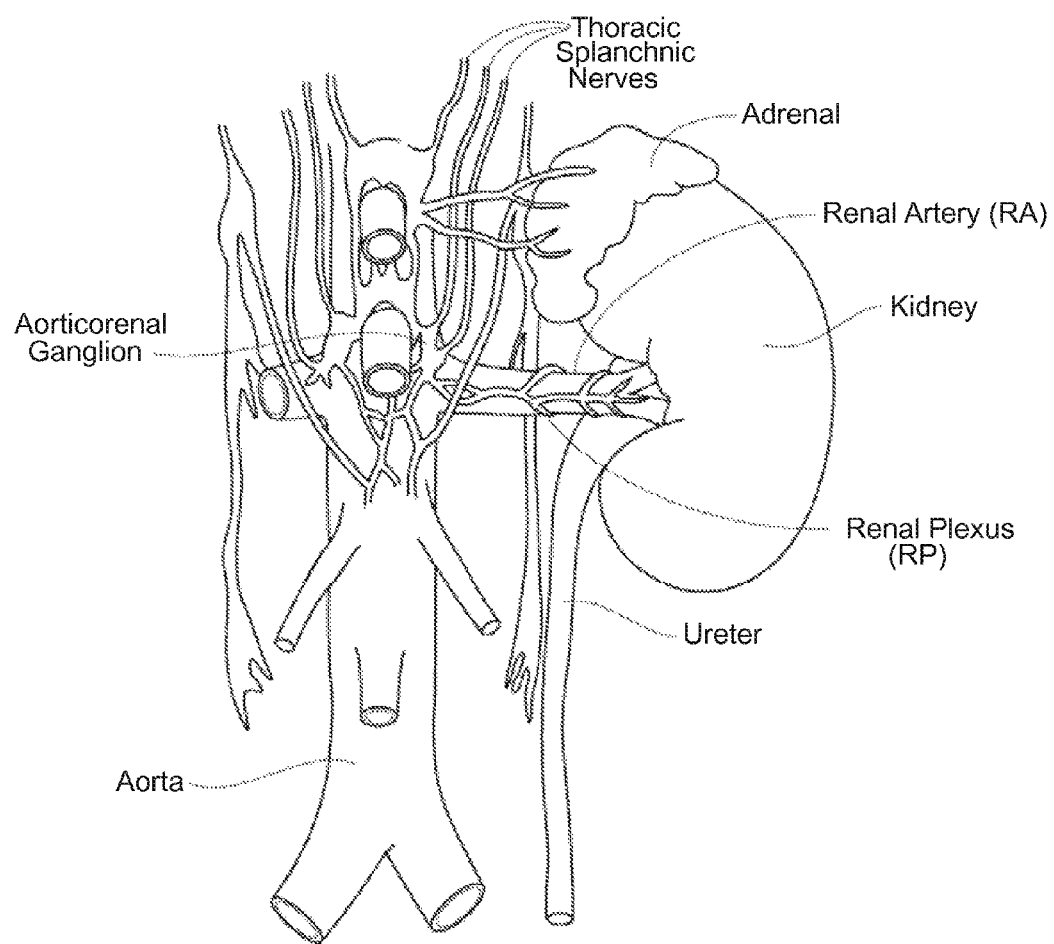
FIG. 7 is an enlarged anatomical view illustrating nerves innervating a left kidney to form a renal plexus surrounding a left renal artery.

As FIG. 7 shows, the kidney is innervated by the renal plexus, which is intimately associated with the renal artery. The renal plexus is an autonomic plexus that surrounds the renal artery and is embedded within the adventitia of the renal artery. The renal plexus extends along the renal artery until it arrives at the substance of the kidney. Fibers contributing to the renal plexus arise from the celiac ganglion, the superior mesenteric ganglion, the aorticorenal ganglion and the aortic plexus. The renal plexus, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus and are distributed to the renal vasculature.

C. Renal Sympathetic Neural Activity

Messages travel through the SNS in a bidirectional flow. Efferent messages may trigger changes in different parts of the body simultaneously. For example, the SNS may accelerate heart rate, widen bronchial passages, decrease motility (movement) of the large intestine, constrict blood vessels, increase peristalsis in the esophagus, cause pupil dilation, cause piloerection (i.e., goose bumps), cause perspiration (i.e., sweating), and raise blood pressure. Afferent messages carry signals from various organs and sensory receptors in the body to other organs and, particularly, the brain.

Hypertension, heart failure, and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing overactivity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine spillover rates in patients with essential hypertension, particularly so in young hypertensive subjects, which in concert with increased norepinephrine spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced SNS overactivity.

Activation of cardiorenal sympathetic nerve activity is even more pronounced in heart failure, as demonstrated by an exaggerated increase of norepinephrine overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end-stage renal disease are characterized by heightened sympathetic nervous activation. In patients with end-stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that afferent signals originating from the diseased kidneys are major contributors to initiating and sustaining elevated central sympathetic outflow in this patient group. This facilitates the occurrence of the well-known adverse consequences of chronic sympathetic overactivity, such as hypertension, left ventricular hypertrophy, ventricular arrhythmias, sudden cardiac death, insulin resistance, diabetes, and metabolic syndrome.

(i) Renal Sympathetic Efferent Nerve Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). However, the current pharmacologic strategies have significant limitations including limited efficacy, compliance issues, side effects, and others.

(ii) Renal Afferent Nerve Activity

Figure 8:
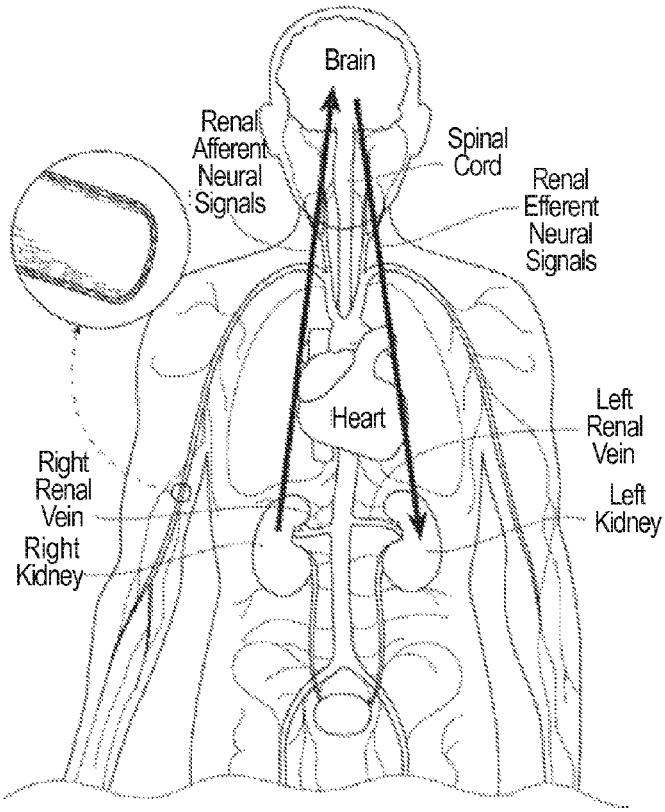
FIGS. 8 and 9 are anatomical and conceptual views, respectively, illustrating a human body including a brain and kidneys and neural efferent and afferent communication between the brain and kidneys.
Figure 9:
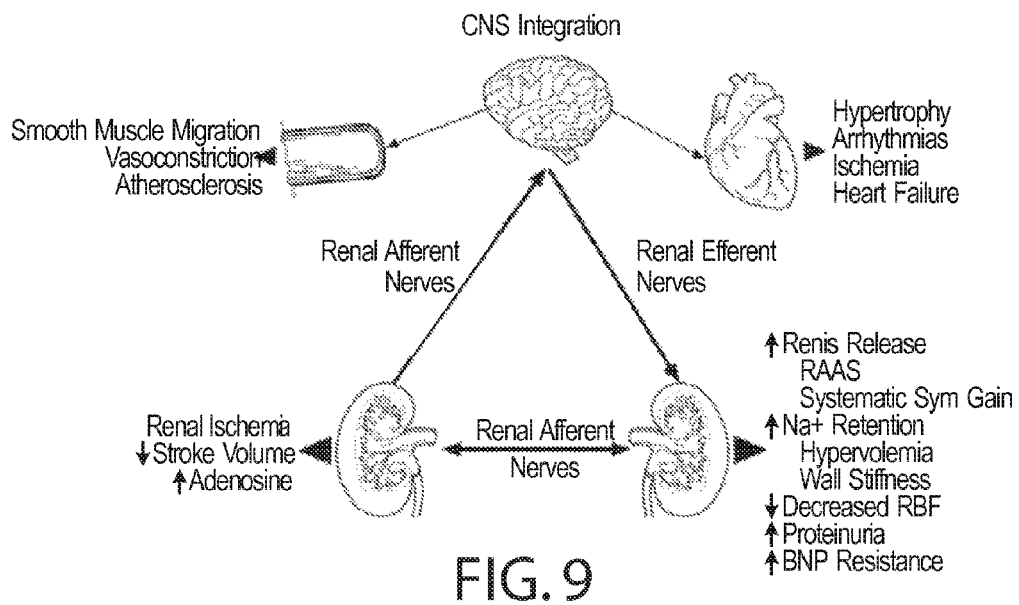

The kidneys communicate with integral structures in the CNS via renal afferent nerves. Several forms of "renal injury" may induce activation of afferent signals. For example, renal ischemia, reduction in stroke volume or renal blood flow, or an abundance of adenosine enzyme may trigger activation of afferent neural communication. As shown in FIGS. 8 and 9, this afferent communication might be from the kidney to the brain or might be from one kidney to the other kidney (via the CNS). These afferent signals are centrally integrated and may result in increased sympathetic outflow. This sympathetic drive is directed toward the kidneys, thereby activating the RAAS and inducing increased renin secretion, sodium retention, volume retention, and vasoconstriction. Central sympathetic overactivity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (a) modulation of tissue with efferent sympathetic nerves will reduce inappropriate renin release, salt retention, and reduction of renal blood flow, and (b) modulation of tissue with afferent nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

D. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end-stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 6. For example, as previously discussed, a reduction in central sympathetic drive may reduce the insulin resistance that afflicts people with metabolic syndrome and Type II diabetes. Additionally, patients with osteoporosis are also sympathetically activated and might also benefit from the down regulation of sympathetic drive that accompanies renal denervation.

E. Achieving Intravascular Access to the Renal Artery

Figure 10:
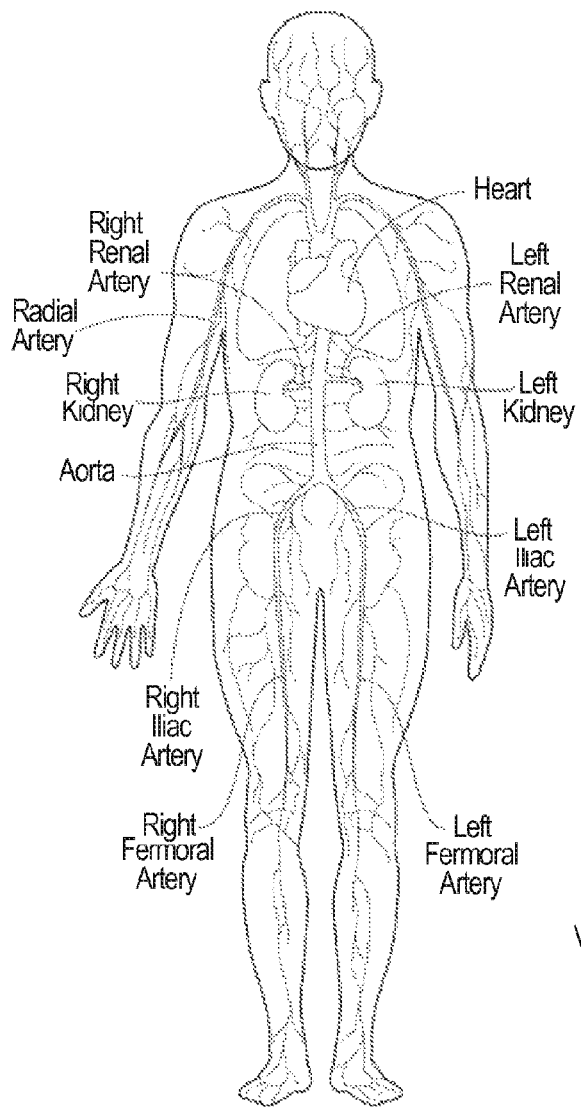
FIGS. 10 and 11 are anatomic views illustrating, respectively, an arterial vasculature and a venous vasculature of a human.

In accordance with the present technology, neuromodulation of a left and/or right renal plexus, which is intimately associated with a left and/or right renal artery, may be achieved through intravascular access. As FIG. 10 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 11:
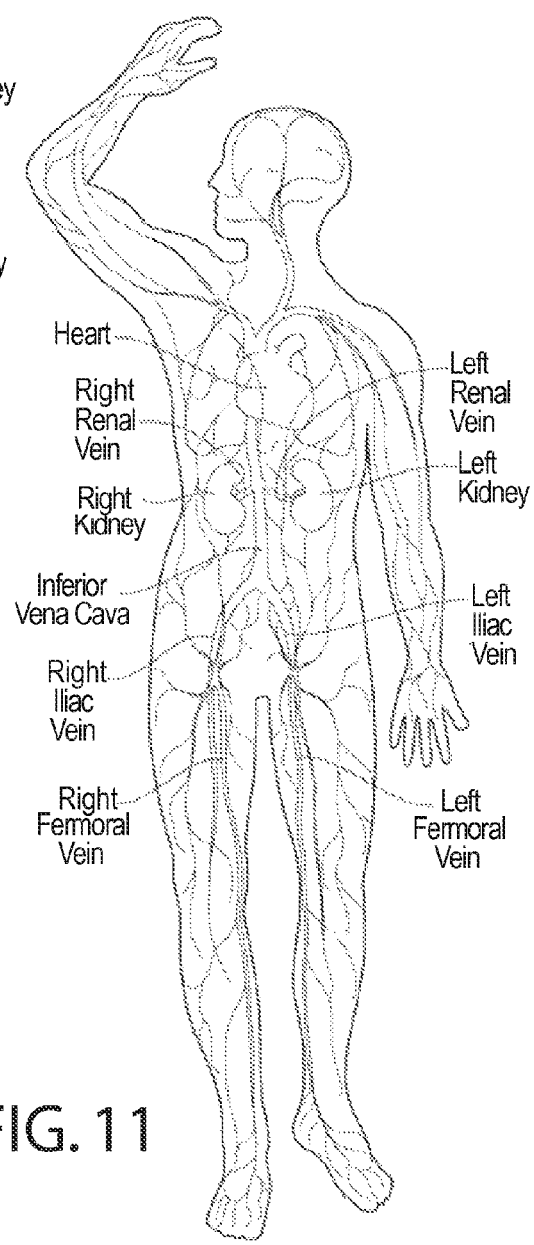

As FIG. 11 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

F. Properties and Characteristics of the Renal Vasculature

Since neuromodulation of a left and/or right renal plexus may be achieved in accordance with embodiments of the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic, and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems, and methods for achieving renal neuromodulation via intravascular access can account for these and other aspects of renal arterial anatomy and its variations across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes a cryotherapeutic device, consistent positioning, appropriate contact force applied by the cryotherapeutic device to the vessel wall, and adhesion between the cryo-applicator and the vessel wall can be important for predictability. However, navigation can be impeded by the tight space within a renal artery, as well as tortuosity of the artery. Furthermore, establishing consistent contact can be complicated by patient movement, respiration, and/or the cardiac cycle because these factors may cause significant movement of the renal artery relative to the aorta, and the cardiac cycle may transiently distend the renal artery (i.e., cause the wall of the artery to pulse).

After accessing a renal artery and facilitating stable contact between a neuromodulatory apparatus and a luminal surface of the artery, nerves in and around the adventitia of the artery can be modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy can be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery can be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus can be configured to allow for adjustable positioning and repositioning of an energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesions likely resulting from a continuous circumferential treatment may be potentially related to renal artery stenosis. Therefore, the formation of more complex lesions along a longitudinal dimension of the renal artery via the cryotherapeutic devices and/or repositioning of the neuromodulatory apparatus to multiple treatment locations may be desirable. It should be noted, however, that a benefit of creating a circumferential ablation may outweigh the potential of renal artery stenosis, or the risk may be mitigated with certain embodiments or in certain patients, and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery can also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time can be avoided in some cases to prevent injury to the kidney such as ischemia. It can be beneficial to avoid occlusion altogether or, if occlusion is beneficial, to limit the duration of occlusion, for example, to 2-5 minutes.

Based on the above-described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity, (b) distensibility, stiffness, and modulus of elasticity of the vessel wall, (c) peak systolic, end-diastolic blood flow velocity, as well as the mean systolic-diastolic peak blood flow velocity, and mean/max volumetric blood flow rate, (d) specific heat capacity of blood and/or of the vessel wall, thermal conductivity of blood and/or of the vessel wall, and/or thermal convectivity of blood flow past a vessel wall treatment site and/or radiative heat transfer, (e) renal artery motion relative to the aorta induced by respiration, patient movement, and/or blood flow pulsatility, and (f) the takeoff angle of a renal artery relative to the aorta. These properties will be discussed in greater detail with respect to the renal arteries. However, dependent on the apparatus, systems, and methods utilized to achieve renal neuromodulation, such properties of the renal arteries also may guide and/or constrain design characteristics.

As noted above, an apparatus positioned within a renal artery can conform to the geometry of the artery. Renal artery vessel diameter, DRA, typically is in a range of about 2-10 mm, with most of the patient population having a DRA of about 4 mm to about 8 mm and an average of about 6 mm.

Renal artery vessel length, LRA, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite intima-media thickness (i.e., the radial outward distance from the artery's luminal surface to the adventitia containing target neural structures) also is notable and generally is in a range of about 0.5-2.5 mm, with an average of about 1.5 mm. Although a certain depth of treatment can be important to reach the target neural fibers, the treatment typically is not too deep (e.g., the treatment can be less than about 5 mm from inner wall of the renal artery) so as to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as four includes cranially with respiratory excursion. This may impart significant motion to the renal artery connecting the aorta and the kidney. Accordingly, the neuromodulatory apparatus can have a unique balance of stiffness and flexibility to maintain contact between a cryo-applicator or another thermal treatment element and the vessel wall during cycles of respiration. Furthermore, the takeoff angle between the renal artery and the aorta may vary significantly between patients, and also may vary dynamically within a patient (e.g., due to kidney motion). The takeoff angle generally may be in a range of about 30°-135°.

The foregoing embodiments of cryotherapeutic devices are configured to accurately position the cryo-applicators in and/or near the renal artery and/or renal ostium via a femoral approach, transradial approach, or another suitable vascular approach. In any of the foregoing embodiments described above with reference to FIGS. 1-5B, single balloons can be configured to be inflated to diameters of about 3 mm to about 8 mm, and multiple balloons can collectively be configured to be inflated to diameters of about 3 mm to about 8 mm, and in several embodiments 4 mm to 8 mm. Additionally, in any of the embodiments described herein with reference to FIGS. 1-11, the balloons can individually and/or collectively have a length of about 3 mm to about 15 mm, and in several embodiments about 5 mm. For example, several specific embodiments of the devices described with reference to in FIGS. 1-5B can have a 5 mm long balloon that is configured to be inflated to a diameter of 4 mm to 8 mm. The shaft of the devices described above with reference to any of the embodiments described with reference to FIGS. 1-5B can be sized to fit within a 6 Fr sheath, such as a 4 Fr shaft size.

V. Conclusion

The above detailed descriptions of embodiments of the present technology are for purposes of illustration only and are not intended to be exhaustive or to limit the present technology to the precise form(s) disclosed above. Various equivalent modifications are possible within the scope of the present technology, as those skilled in the relevant art will recognize. For example, while stages may be presented in a given order, alternative embodiments may perform stages in a different order. The various embodiments described herein and elements thereof may also be combined to provide further embodiments. In some cases, well-known structures and functions have not been shown or described in detail to avoid unnecessarily obscuring the description of embodiments of the present technology.

Where the context permits, singular or plural terms may also include the plural or singular terms, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout the disclosure to mean including at least the recited feature(s) such that any greater number of the same feature(s) and/or additional types of other features are not precluded. It will also be appreciated that various modifications may be made to the described embodiments without deviating from the present technology. Further, while advantages associated with certain embodiments of the present technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

We claim:

1. A method of forming a balloon from an extruded integral shaft having a plurality of lumens along the shaft, the plurality of lumens including at least a first lumen and a second lumen, the method comprising:
    positioning a distal portion of the shaft in a mold configured to define an outer surface of the balloon;
    clamping a first end region of the distal portion with the mold;
    rotating the mold relative to the shaft thereby forming a twisted distal portion of the shaft; and
    forming the balloon along the twisted distal portion, wherein the balloon is configured to deliver therapeutically effective cryogenic cooling to a treatment site.

2. The method of claim 1 wherein the first lumen defines a first fluid passageway and the second lumen defines a second fluid passageway independent of the first fluid passageway.

3. The method of claim 1 wherein the extruded integral shaft includes a third lumen extending along the shaft, wherein the third lumen is positioned radially inward from the first and second lumens and configured to receive a guide wire.

4. The method of claim 1 wherein forming the balloon comprises plastically enlarging the twisted distal portion of the first and second lumens.

5. The method of claim 1 wherein forming the twisted distal portion includes twisting at least a section of the shaft distal to the clamped first end region.

6. The method of claim 1 wherein the balloon includes an outer surface that is substantially continuous at transverse cross-sections of the balloon.

7. The method of claim 1 wherein the twisted distal portion terminates at a proximal end region of the balloon.

8. A method of forming an inflatable body from an extruded integral shaft having at least first and second lumens extending along the shaft substantially parallel to each other for at least a portion of the shaft, the method comprising:
    positioning a distal portion of the shaft in a mold configured to define an outer surface of the inflatable body;
    clamping a first end region of the distal portion with the mold;
    rotating the mold relative to the shaft thereby twisting a distal portion of the shaft such that the first lumen has a first helical portion and the second lumen has a second helical portion intertwined with the first helical portion; and plastically enlarging the intertwined first and second helical portions to form the inflatable body, wherein the inflatable body is configured to deliver therapeutically effective cryogenic cooling to a treatment site.

9. The method of claim 8 wherein the shaft further comprises a polymeric material, the shaft having a guide wire lumen positioned centrally between the at least first and second lumens, and wherein:
plastically enlarging the intertwined first and second helical portions comprises heating, pressurizing, and stretching the distal portion of the shaft; and
the method further comprises—
supporting the distal portion of the shaft with a mandrel extending through the guide wire lumen during twisting of the distal portion,
clamping the shaft at first and second end regions of the distal portion such that the first and second helical portions extend between the first and second end regions and the first and second lumens extend substantially straight proximally from the distal portion, and
applying heat to the distal portion as the distal portion of the shaft is twisted.

10. The method of claim 8 wherein the shaft has at least four lumens extending at least substantially parallel to one another along the shaft, and wherein the first and second lumens are two of the at least four lumens.

11. The method of claim 8 wherein the shaft comprises a guide wire lumen extending between the first and second lumens.

12. The method of claim 11 wherein twisting the distal portion of the shaft comprises:
supporting the shaft with a mandrel removably disposed within the guide wire lumen in at least the distal section;
clamping the shaft at a first end region of the distal portion; and
twisting a second end region of the distal portion, wherein a clamp pressure at the first end region is configured to retain the first end region during twisting without binding the shaft to the mandrel.

13. The method of claim 8 wherein plastically enlarging the first and second helical portions of the first and second lumens comprises:
stretch blow molding at least a length of the distal portion to form the inflatable body; and
maintaining pressure within the first and second lumens during the stretch blow molding.

14. The method of claim 8 wherein plastically enlarging the first and second helical portions of the first and second lumens comprises forming an inflatable body having a length of approximately 8-15mm and an outer diameter of approximately 3-8 mm in a deployed state.

15. The method of claim 8 wherein plastically enlarging the first and second helical portions of the first and second lumens comprises forming an inflatable body having an outer diameter of less than 2 mm in a delivery state.

* * * * *